US008285486B2

(12) United States Patent
Martin et al.

(10) Patent No.: US 8,285,486 B2
(45) Date of Patent: *Oct. 9, 2012

(54) METHODS OF DETERMINING RELATIVE GENETIC LIKELIHOODS OF AN INDIVIDUAL MATCHING A POPULATION

(75) Inventors: Lucas Martin, Arlington, VA (US); Eduardas Valaitis, Arlington, VA (US)

(73) Assignee: DNA Tribes LLC, Arlington, VA (US)

( * ) Notice: Subject to any disclaimer, the term of this patent is extended or adjusted under 35 U.S.C. 154(b) by 160 days.

This patent is subject to a terminal disclaimer.

(21) Appl. No.: 12/108,327

(22) Filed: Apr. 23, 2008

(65) Prior Publication Data

US 2008/0255768 A1    Oct. 16, 2008

Related U.S. Application Data

(63) Continuation-in-part of application No. 11/621,646, filed on Jan. 10, 2007, now abandoned.

(60) Provisional application No. 60/766,426, filed on Jan. 18, 2006.

(51) Int. Cl.
*G01N 33/48* (2006.01)

(52) U.S. Cl. .......................................... 702/19

(58) Field of Classification Search ..................... 702/19
See application file for complete search history.

(56) References Cited

U.S. PATENT DOCUMENTS

| 2003/0134285 | A1* | 7/2003 | Oefner et al. ..................... 435/6 |
| 2003/0224394 | A1 | 12/2003 | Schadt et al. |
| 2004/0126782 | A1* | 7/2004 | Holden et al. .................. 702/20 |
| 2004/0229231 | A1* | 11/2004 | Frudakis et al. .................. 435/6 |
| 2005/0009069 | A1 | 1/2005 | Liu et al. |
| 2006/0008815 | A1 | 1/2006 | Rosenfeld et al. |
| 2007/0178500 | A1 | 8/2007 | Martin et al. |

FOREIGN PATENT DOCUMENTS

WO    WO 2004/061616    *   7/2004

OTHER PUBLICATIONS

Foreman et al. (J. R. Statist. Soc. A (1997), vol. 160, Part 3, pp. 429-469).*
Shriver et al. (Am. J. Hum. Genet. 60:957-964, 1997).*
Lowe et al. (Forensic Science International 119 (2001) 17-22).*
Friedman et al. (Journal of Computational Biology, vol. 7, Nos. 3/4, p. 601-620, 2000).*
Pritchard et al. (Genetics, vol. 155, p. 945-959, Jun. 2000).*
Michelson (The Biostatistics Cookbook, Kluwer Academic Publishers, Dordrecht, NL 1996, 172 pages).*
Nasidze et al. (European Journal of Human Genetics, vol. 9, p. 267-272, 2001).*
IPRP, Written Opinion and ISR in related PCT Application PCT/US2007/060605.
Forensic match calculation methods using OmniPop. See Wikipedia entry printed on Jul. 9, 2009: "http://en.wikipedia.org/wiki/Omnipop" (updated on Feb. 3, 2009).
ENFSI match calculator. See "http://www.str-base.org/" printed on Jul. 9, 2009.
Genetics and Genomics of Core Short Tandem Repeat Loci Used in Human Identity Testing, John M. Butler, Ph.D. Journal of Forensic Sciences, vol. 51, Issue 2, p. 253-265, Mar. 2006, doi: 10.1111/j.1556-4029.2006.00046.x.
Balding, "Estimating Products in Forensic Identification Using DNA Profiles," Journal of the American Statistical Association, vol. 90, No. 431. (Sep. 1995), pp. 839-844.
Balding and Nichols, "DNA Profile Match Probability Calculation: How to Allow for Population Stratification, Relatedness, . . ." Forensic Science Intl., 1994, pp. 125-140.
Harmon, "Seeking Ancestry in DNA Ties Uncovered by Tests," NY Times, Apr. 12, 2006.
Jun. 19, 2009 Action/Restriction Requirement in parent U.S. Appl. No. 11/621,646.
Oct. 7, 2009 Office Action in parent U.S. Appl. No. 11/621,646.
Afrrican Ancestry website, http://www.africanancestry.com, published on the web and accessed on Mar. 12, 2007 (see document).
DNA Print and ancestrybydna websites, www.dnaprint.com and www.ancestrybydna.com, published on the web and accessed on Mar. 12, 2007 (see document).
http://www.cstl.nist.gov/biotech/strbase/populationdata.htm, published on the web and accessed on May 14, 2008 (see document).
http://www.str-base.org/, accessed on the web and accessed on May 14, 2008 (see document).
ENFSI DNA WG STR Population database, "http://www.str-base.org/" printed on Jul. 9, 2009 (see document).
Office Action mailed May 13, 2010 in parent U.S. Appl. No. 11/621,646.
May 13, 2010 Office Action in related U.S. Appl. No. 11/621,646.
Oct. 27, 2010 Office Action in related U.S. Appl. No. 11/621,646.

* cited by examiner

*Primary Examiner* — Jerry Lin
(74) *Attorney, Agent, or Firm* — Kristina Casdellano; Castellano PLLC

(57) ABSTRACT

Provided are methods of determining an individual's relative likelihood of having a genetic match with one or more local populations as compared to a generic index population. Also provided are systems, apparatuses, kits, and machine-readable medium relating to such methods. The methods may be used for example, to identify an individual's or individual's ancestor's most likely geographic origin, or to identify the breed, species, kingdom, etc. of an organism.

45 Claims, 38 Drawing Sheets

FIG. 6
American Indian Regions
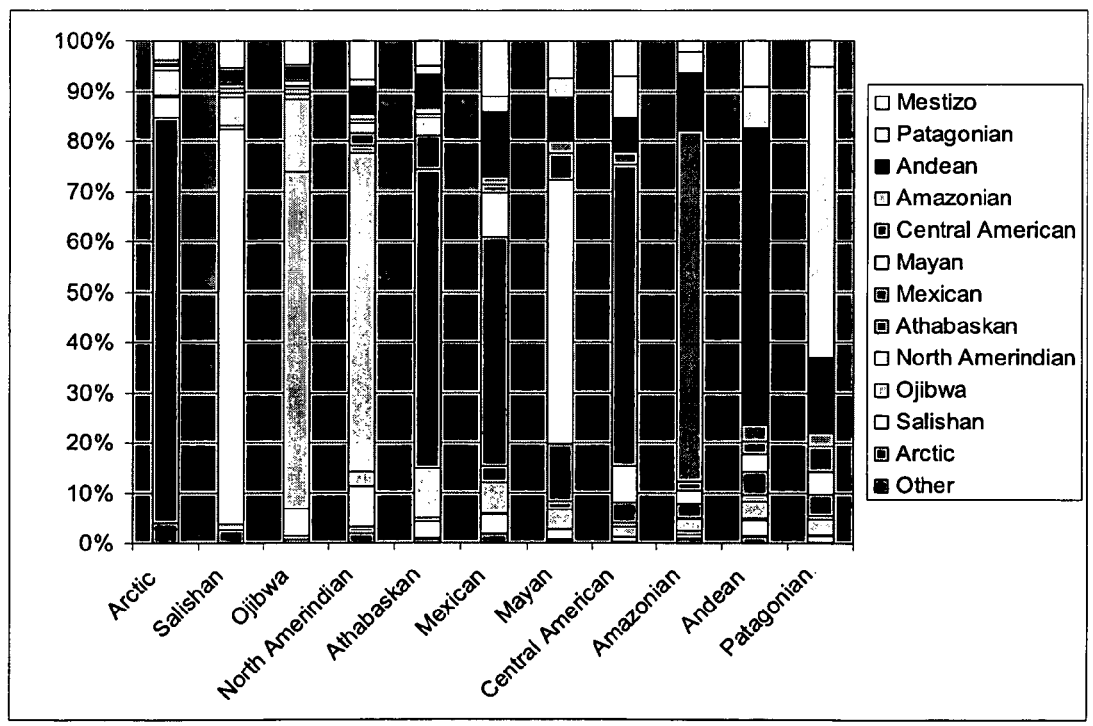

FIG. 7
European and Near Eastern Regions
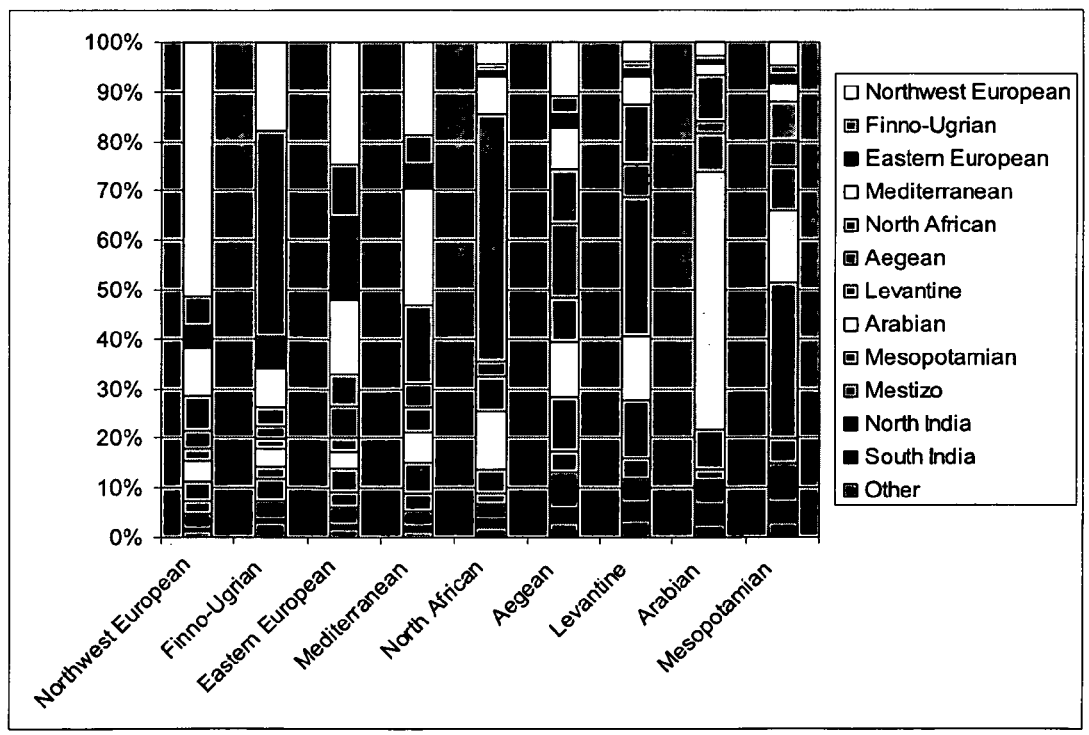

FIG. 8
Sub-Saharan African and Central and South Asian Regions
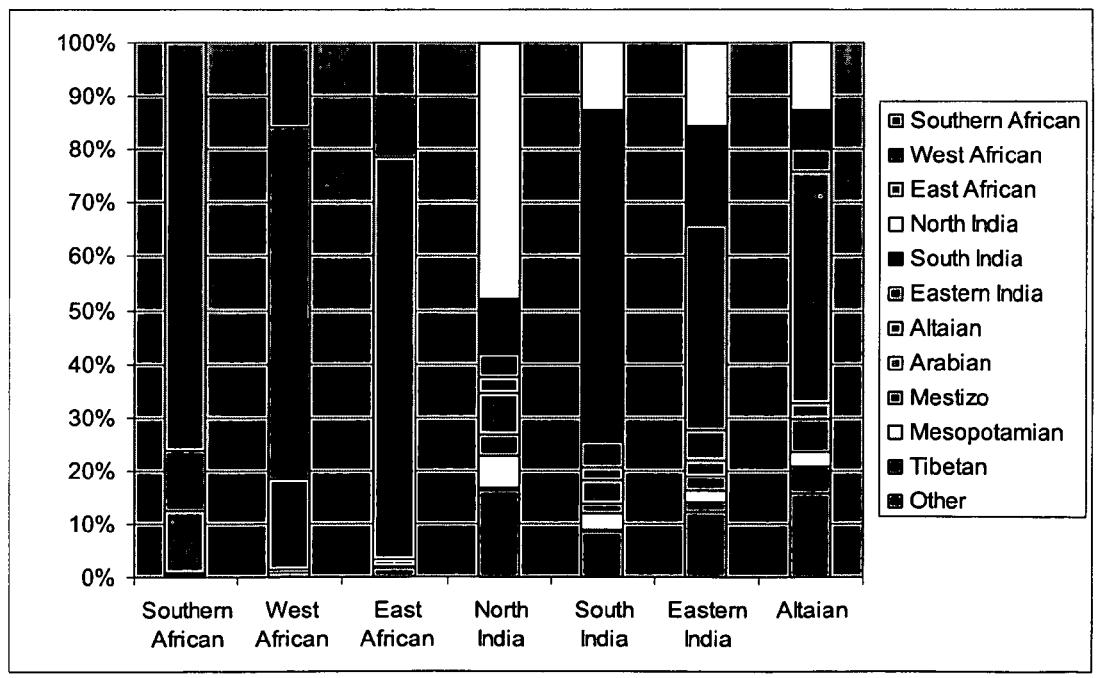

FIG. 9
East Asian and Pacific Populations
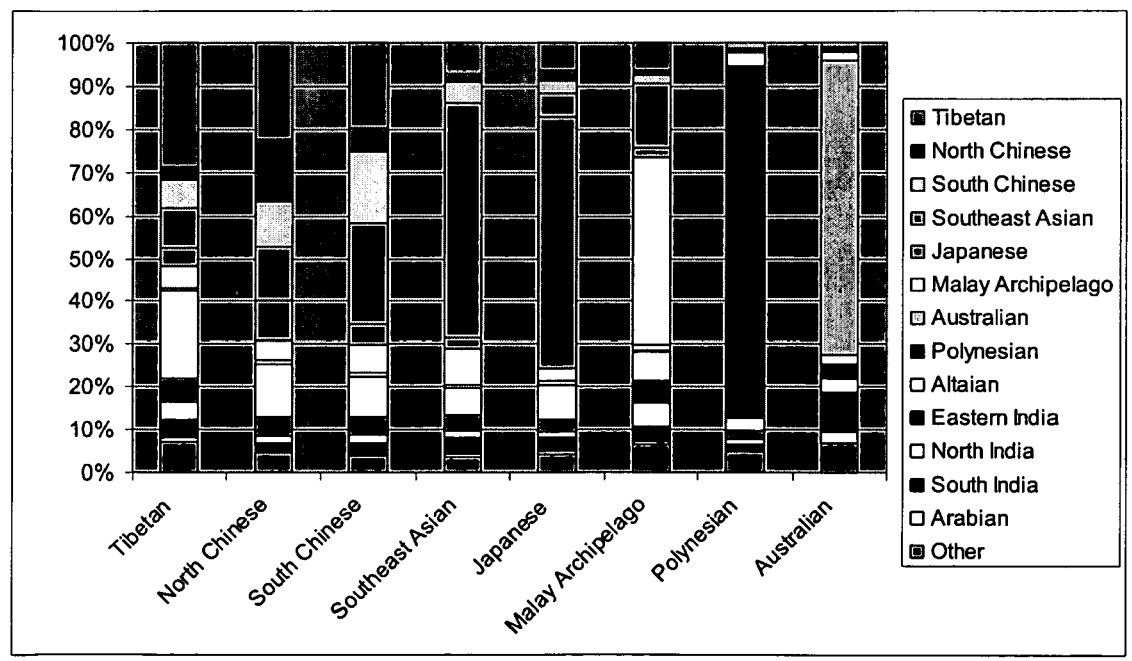

FIG. 11

Caucasian (United States) (World Regions)

|  | 5% | 25% | 50% | 75% | 95% |
|---|---|---|---|---|---|
|  | (very low) | (ordinary) | (ordinary) | (ordinary) | (very high) |
| Northwest European | 1.90 | 26.31 | 182.19 | 1,423.14 | 25,825.32 |
| Mediterranean | 1.43 | 21.15 | 136.15 | 975.53 | 17,564.77 |
| Eastern European | 0.96 | 15.28 | 98.03 | 794.92 | 12,872.07 |
| Aegean | 1.93 | 17.26 | 84.68 | 468.46 | 5,950.63 |
| Levantine | 0.86 | 9.19 | 50.68 | 293.52 | 4,245.86 |
| Finno-Ugrian | 0.35 | 6.27 | 45.22 | 321.29 | 6,272.69 |
| Mesopotamian | 0.94 | 8.18 | 39.86 | 218.51 | 2,623.37 |
| North African | 0.32 | 4.83 | 35.58 | 280.34 | 5,664.06 |
| Arabian | 0.40 | 4.45 | 26.37 | 163.74 | 2,198.13 |
| Mestizo | 0.48 | 3.99 | 16.32 | 73.37 | 636.78 |
| North India | 0.57 | 3.51 | 12.45 | 45.16 | 283.76 |
| South India | 0.04 | 0.28 | 1.03 | 4.28 | 36.01 |
| Altaian | 0.02 | 0.18 | 0.66 | 2.23 | 11.47 |
| Eastern India | 0.02 | 0.14 | 0.48 | 1.52 | 8.55 |
| East African | 0.00 | 0.00 | 0.01 | 0.27 | 16.74 |
| Tibetan | 0.00 | 0.00 | 0.01 | 0.06 | 0.58 |
| Malay Archipelago | 0.00 | 0.00 | 0.01 | 0.03 | 0.29 |
| Australian | 0.00 | 0.00 | 0.00 | 0.01 | 0.16 |
| West African | 0.00 | 0.00 | 0.00 | 0.05 | 4.24 |
| Southeast Asian | 0.00 | 0.00 | 0.00 | 0.01 | 0.13 |
| South Chinese | 0.00 | 0.00 | 0.00 | 0.00 | 0.08 |
| Southern African | 0.00 | 0.00 | 0.00 | 0.01 | 1.58 |
| Andean | 0.00 | 0.00 | 0.00 | 0.00 | 0.18 |
| Salishan | 0.00 | 0.00 | 0.00 | 0.00 | 0.08 |
| North Amerindian | 0.00 | 0.00 | 0.00 | 0.00 | 0.08 |
| Mexican | 0.00 | 0.00 | 0.00 | 0.00 | 0.06 |
| North Chinese | 0.00 | 0.00 | 0.00 | 0.00 | 0.03 |
| Arctic | 0.00 | 0.00 | 0.00 | 0.00 | 0.03 |
| Mayan | 0.00 | 0.00 | 0.00 | 0.00 | 0.02 |
| Japanese | 0.00 | 0.00 | 0.00 | 0.00 | 0.02 |
| Patagonian | 0.00 | 0.00 | 0.00 | 0.00 | 0.03 |
| Athabaskan | 0.00 | 0.00 | 0.00 | 0.00 | 0.01 |
| Central American | 0.00 | 0.00 | 0.00 | 0.00 | 0.01 |
| Polynesian | 0.00 | 0.00 | 0.00 | 0.00 | 0.00 |
| Ojibwa | 0.00 | 0.00 | 0.00 | 0.00 | 0.00 |
| Amazonian | 0.00 | 0.00 | 0.00 | 0.00 | 0.00 |

FIG. 12

Caucasian (United States) (Europa Sub-Regions)

|  | 5.00% | 25.00% | 50.00% | 75.00% | 95.00% |
|---|---|---|---|---|---|
|  | (very low) | (ordinary) | (ordinary) | (ordinary) | (very high) |
| Norse | 1.79 | 25.02 | 192.90 | 1,350.58 | 22,996.43 |
| Celtic | 1.38 | 23.26 | 183.23 | 1,352.04 | 26,815.71 |
| Germanic | 1.44 | 22.02 | 170.02 | 1,187.72 | 18,656.73 |
| Italian | 1.72 | 23.61 | 169.77 | 1,096.99 | 13,686.63 |
| Spanish | 1.31 | 20.37 | 155.08 | 1,091.29 | 18,701.38 |
| Portuguese | 1.34 | 18.51 | 146.18 | 1,077.58 | 18,472.18 |
| Balkan | 1.19 | 17.88 | 131.88 | 974.70 | 13,581.44 |
| Polish | 0.78 | 12.15 | 94.24 | 711.43 | 11,324.42 |
| Greek | 0.97 | 13.35 | 82.90 | 545.47 | 6,717.89 |
| Russian | 0.64 | 10.19 | 77.88 | 572.29 | 10,102.97 |
| Basque | 0.28 | 6.38 | 63.90 | 583.43 | 11,913.49 |
| Ashkenazi | 0.36 | 6.20 | 53.14 | 403.26 | 7,495.74 |
| Finno-Ugrian | 0.46 | 6.75 | 47.97 | 341.42 | 6,421.41 |

FIG. 13

African-American (United States)

| | 5% | 25% | 50% | 75% | 95% |
|---|---|---|---|---|---|
| | (very low) | (ordinary) | (ordinary) | (ordinary) | (very high) |
| West African | 5.93 | 1,150.84 | 53,876.48 | 2,792,606.95 | 1,621,469,999.23 |
| East African | 9.30 | 1,237.82 | 45,452.08 | 1,613,934.30 | 450,063,793.37 |
| Southern African | 0.81 | 265.59 | 17,383.57 | 880,528.46 | 450,255,906.57 |
| Arabian | 1.28 | 17.54 | 108.66 | 713.26 | 13,696.12 |
| North African | 0.36 | 10.23 | 94.59 | 833.15 | 24,259.09 |
| Levantine | 0.24 | 3.85 | 24.14 | 146.13 | 2,000.81 |
| Mestizo | 0.28 | 2.79 | 12.43 | 57.32 | 592.13 |
| Aegean | 0.11 | 1.45 | 9.27 | 53.45 | 748.59 |
| Northwest European | 0.04 | 0.81 | 6.25 | 51.32 | 1,060.66 |
| Mesopotamian | 0.05 | 0.74 | 4.44 | 25.64 | 331.69 |
| Mediterranean | 0.03 | 0.61 | 4.36 | 34.92 | 712.25 |
| North India | 0.04 | 0.31 | 1.58 | 8.19 | 77.68 |
| Eastern European | 0.00 | 0.11 | 0.89 | 8.58 | 200.30 |
| Finno-Ugrian | 0.00 | 0.04 | 0.37 | 3.38 | 77.60 |
| South India | 0.01 | 0.06 | 0.35 | 1.99 | 18.25 |
| Altaian | 0.00 | 0.01 | 0.03 | 0.16 | 1.35 |
| Eastern India | 0.00 | 0.00 | 0.01 | 0.04 | 0.41 |
| Tibetan | 0.00 | 0.00 | 0.00 | 0.01 | 0.08 |
| Australian | 0.00 | 0.00 | 0.00 | 0.00 | 0.06 |
| Malay Archipelago | 0.00 | 0.00 | 0.00 | 0.00 | 0.02 |
| Arctic | 0.00 | 0.00 | 0.00 | 0.00 | 0.26 |
| Salishan | 0.00 | 0.00 | 0.00 | 0.00 | 0.16 |
| Andean | 0.00 | 0.00 | 0.00 | 0.00 | 0.05 |
| North Amerindian | 0.00 | 0.00 | 0.00 | 0.00 | 0.08 |
| Mexican | 0.00 | 0.00 | 0.00 | 0.00 | 0.04 |
| Southeast Asian | 0.00 | 0.00 | 0.00 | 0.00 | 0.00 |
| South Chinese | 0.00 | 0.00 | 0.00 | 0.00 | 0.00 |
| Mayan | 0.00 | 0.00 | 0.00 | 0.00 | 0.02 |
| Athabaskan | 0.00 | 0.00 | 0.00 | 0.00 | 0.01 |
| Patagonian | 0.00 | 0.00 | 0.00 | 0.00 | 0.01 |
| Polynesian | 0.00 | 0.00 | 0.00 | 0.00 | 0.00 |
| Central American | 0.00 | 0.00 | 0.00 | 0.00 | 0.00 |
| North Chinese | 0.00 | 0.00 | 0.00 | 0.00 | 0.00 |
| Ojibwa | 0.00 | 0.00 | 0.00 | 0.00 | 0.00 |
| Japanese | 0.00 | 0.00 | 0.00 | 0.00 | 0.00 |
| Amazonian | 0.00 | 0.00 | 0.00 | 0.00 | 0.00 |

FIG. 14

Hispanic (United States)

| | 5% (very low) | 25% (ordinary) | 50% (ordinary) | 75% (ordinary) | 95% (very high) |
|---|---|---|---|---|---|
| Mestizo | 0.87 | 8.47 | 38.02 | 199.42 | 2,623.65 |
| Aegean | 0.14 | 1.25 | 6.36 | 34.55 | 504.01 |
| Levantine | 0.10 | 0.97 | 5.41 | 31.78 | 441.33 |
| Mesopotamian | 0.11 | 0.95 | 5.38 | 27.77 | 300.75 |
| Northwest European | 0.05 | 0.66 | 4.68 | 35.46 | 672.72 |
| Arabian | 0.07 | 0.72 | 4.09 | 23.60 | 339.28 |
| Mediterranean | 0.04 | 0.55 | 3.82 | 27.46 | 591.60 |
| North India | 0.13 | 0.86 | 2.84 | 11.27 | 72.23 |
| Eastern European | 0.02 | 0.33 | 2.41 | 17.60 | 332.84 |
| Finno-Ugrian | 0.02 | 0.25 | 1.94 | 14.74 | 272.57 |
| North African | 0.02 | 0.25 | 1.90 | 14.54 | 320.18 |
| Altaian | 0.02 | 0.17 | 0.67 | 2.35 | 16.60 |
| South India | 0.02 | 0.12 | 0.47 | 1.76 | 12.18 |
| Eastern India | 0.01 | 0.06 | 0.22 | 0.76 | 3.51 |
| Andean | 0.00 | 0.00 | 0.03 | 0.73 | 45.98 |
| Tibetan | 0.00 | 0.01 | 0.03 | 0.13 | 1.25 |
| Mexican | 0.00 | 0.00 | 0.01 | 0.23 | 17.83 |
| North Amerindian | 0.00 | 0.00 | 0.01 | 0.20 | 18.67 |
| East African | 0.00 | 0.00 | 0.01 | 0.16 | 10.16 |
| Malay Archipelago | 0.00 | 0.00 | 0.01 | 0.04 | 0.40 |
| Mayan | 0.00 | 0.00 | 0.00 | 0.10 | 10.52 |
| Salishan | 0.00 | 0.00 | 0.00 | 0.07 | 6.95 |
| Patagonian | 0.00 | 0.00 | 0.00 | 0.11 | 14.53 |
| Australian | 0.00 | 0.00 | 0.00 | 0.01 | 0.15 |
| Southeast Asian | 0.00 | 0.00 | 0.00 | 0.01 | 0.40 |
| South Chinese | 0.00 | 0.00 | 0.00 | 0.01 | 0.29 |
| West African | 0.00 | 0.00 | 0.00 | 0.03 | 2.36 |
| Central American | 0.00 | 0.00 | 0.00 | 0.03 | 3.78 |
| Athabaskan | 0.00 | 0.00 | 0.00 | 0.02 | 1.61 |
| Arctic | 0.00 | 0.00 | 0.00 | 0.01 | 0.85 |
| Southern African | 0.00 | 0.00 | 0.00 | 0.01 | 1.13 |
| North Chinese | 0.00 | 0.00 | 0.00 | 0.00 | 0.10 |
| Japanese | 0.00 | 0.00 | 0.00 | 0.00 | 0.07 |
| Ojibwa | 0.00 | 0.00 | 0.00 | 0.00 | 0.97 |
| Amazonian | 0.00 | 0.00 | 0.00 | 0.00 | 1.07 |
| Polynesian | 0.00 | 0.00 | 0.00 | 0.00 | 0.00 |

FIG. 15

| | | | | | | | | | | |
|---|---|---|---|---|---|---|---|---|---|---|
| OBS1173 | | | | | | | | | | |
| 0 | 1 | 1 | 1 | 1 | 1 | 1 | 1 | 1 | 1 | 1 |
| >8 | 0.001 | 0.003 | 0.014 | 0.001 | 0.001 | 0.003 | 0.001 | 0.003 | 0.001 | 0.036 |
| 9 | 0.001 | 0.003 | 0.0105 | 0.002 | 0.0031 | 0.003 | 0.001 | 0.01 | 0.004 | 0.015 |
| 10 | 0.117 | 0.15 | 0.0894 | 0.128 | 0.1372 | 0.083 | 0.1 | 0.087 | 0.131 | 0.078 |
| 11 | 0.067 | 0.073 | 0.049 | 0.103 | 0.1281 | 0.07 | 0.07 | 0.098 | 0.139 | 0.076 |
| 12 | 0.104 | 0.119 | 0.1224 | 0.101 | 0.1067 | 0.133 | 0.135 | 0.11 | 0.131 | 0.095 |
| 13 | 0.217 | 0.178 | 0.3097 | 0.24 | 0.2226 | 0.273 | 0.26 | 0.305 | 0.169 | 0.265 |
| 14 | 0.221 | 0.199 | 0.2188 | 0.218 | 0.2196 | 0.218 | 0.19 | 0.172 | 0.127 | 0.215 |
| 15 | 0.136 | 0.178 | 0.1573 | 0.134 | 0.1067 | 0.13 | 0.16 | 0.14 | 0.197 | 0.155 |
| 16 | 0.053 | 0.066 | 0.0455 | 0.065 | 0.0701 | 0.055 | 0.075 | 0.062 | 0.061 | 0.049 |
| 17 | 0.017 | 0.028 | 0.0036 | 0.009 | 0.0361 | 0.028 | 0.02 | 0.013 | 0.018 | 0.018 |
| <9 | 0.001 | 0.001 | 0.001 | 0.001 | 0.001 | 0.008 | 0.001 | 0.001 | 0.004 | 0.002 |

FIG. 16

| Locus | Individual | Profile |
|---|---|---|
| D8S1179 | 13 | 13 |
| D21S11 | 30 | 30 |
| D7S820 | 10 | 10 |
| CSF1PO | 12 | 11 |
| D3S1358 | 15 | 16 |
| TH01 | 9.3 | 9 |
| D13S317 | 12 | 12 |
| D16S539 | 11 | 12 |
| VWA | 17 | 17 |
| TPOX | 8 | 8 |
| D18S51 | 12 | 12 |
| D5S818 | 11 | 11 |
| FGA | 21 | 20 |

FIG. 17

| 271 | Basque (Alava, Spain) | 1.54E-11 |
|---|---|---|
| 229 | Sephardic Jewish (Turkey) | 8.98E-12 |
| 290 | Caucasian (Western Australia) | 7.63E-12 |
| 76 | Scottish | 5.59E-12 |
| 160 | Aboriginal (Saskatchewan, Canada) | 5.44E-12 |
| 225 | Caucasian (Capital Territory, Australia) | 5.31E-12 |
| 154 | Jewish (Israel) | 4.59E-12 |
| 52 | Caucasian | 4.48E-12 |
| 289 | Caucasian (Queensland, Australia) | 4.46E-12 |
| 231 | Sicilian (Italy) | 4.31E-12 |
| 294 | German | 4.23E-12 |

FIG. 23

| Locus | Allele 1 | Allele 2 |
|---|---|---|
| Amel | X | Y |
| D3S1358 | 15 | 15 |
| TH01 | 8 | 9 |
| D21S11 | 27 | 29 |
| D18S51 | 17 | 18 |
| D5S818 | 11 | 13 |
| D13S317 | 12 | 12 |
| D7S820 | 10 | 12 |
| D16S539 | 10 | 13 |
| CSF1PO | 12 | 13 |
| vWA | 18 | 19 |
| D8S1179 | 12 | 13 |
| TPOX | 10 | 10 |
| FGA | 23 | 31.2 |

FIG. 25
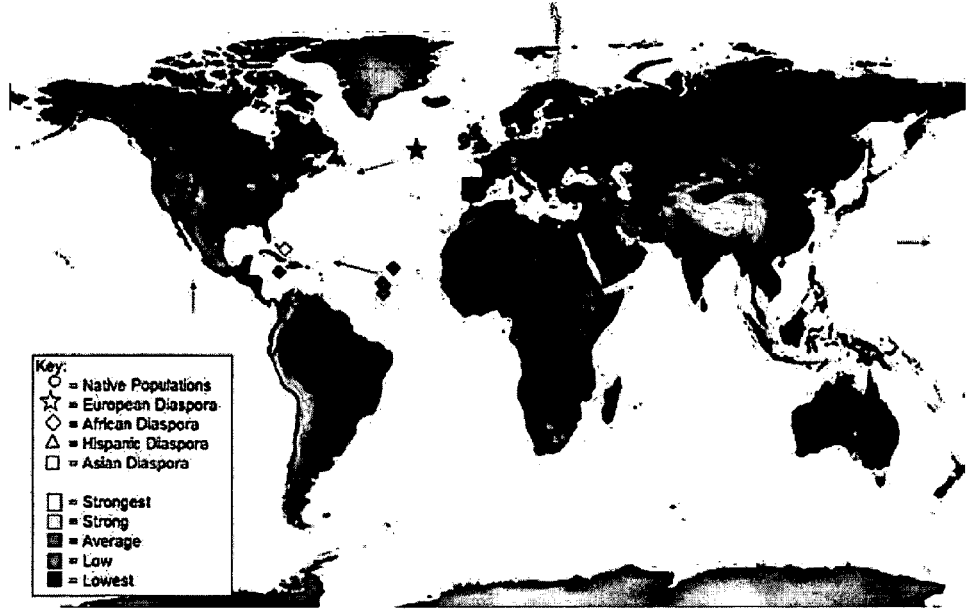
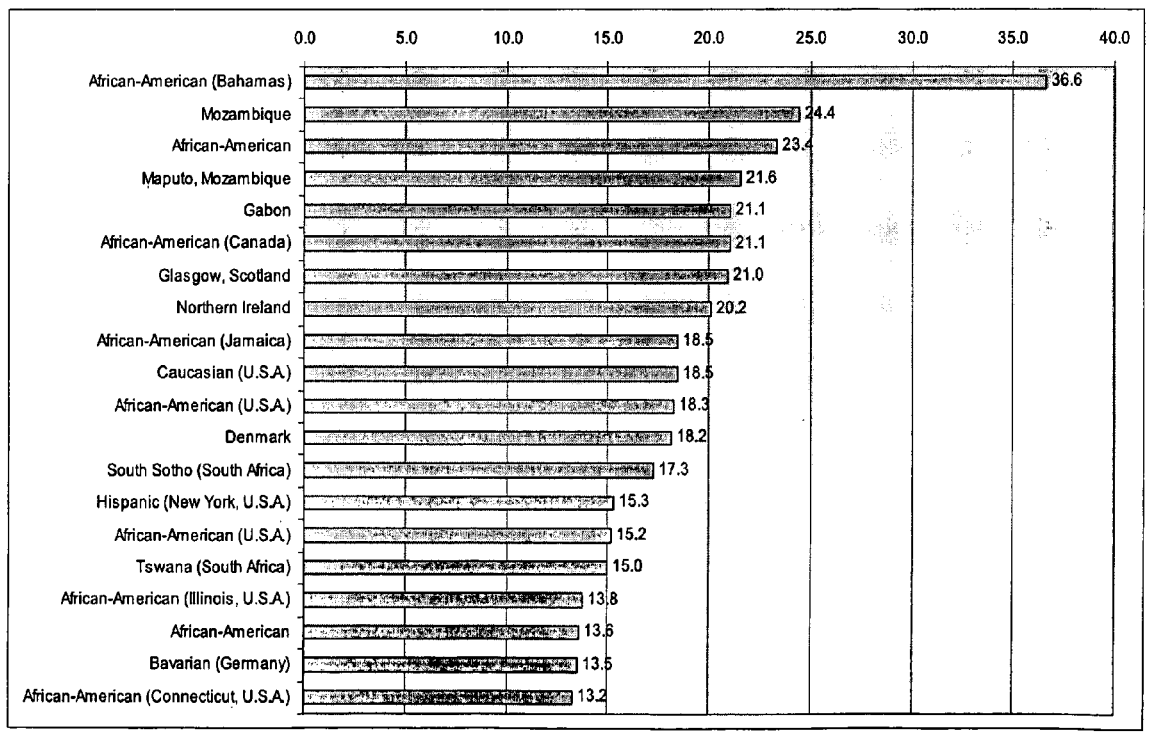

FIG. 26
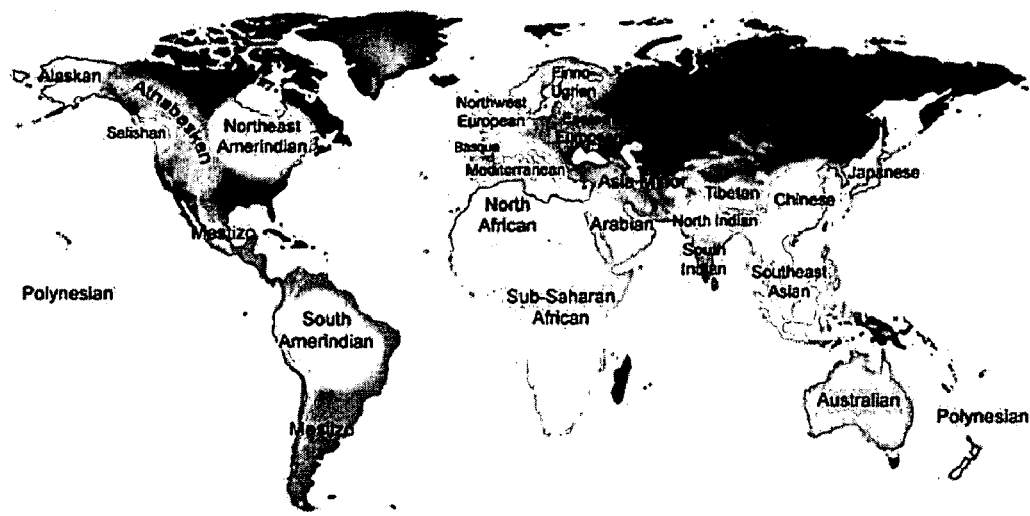
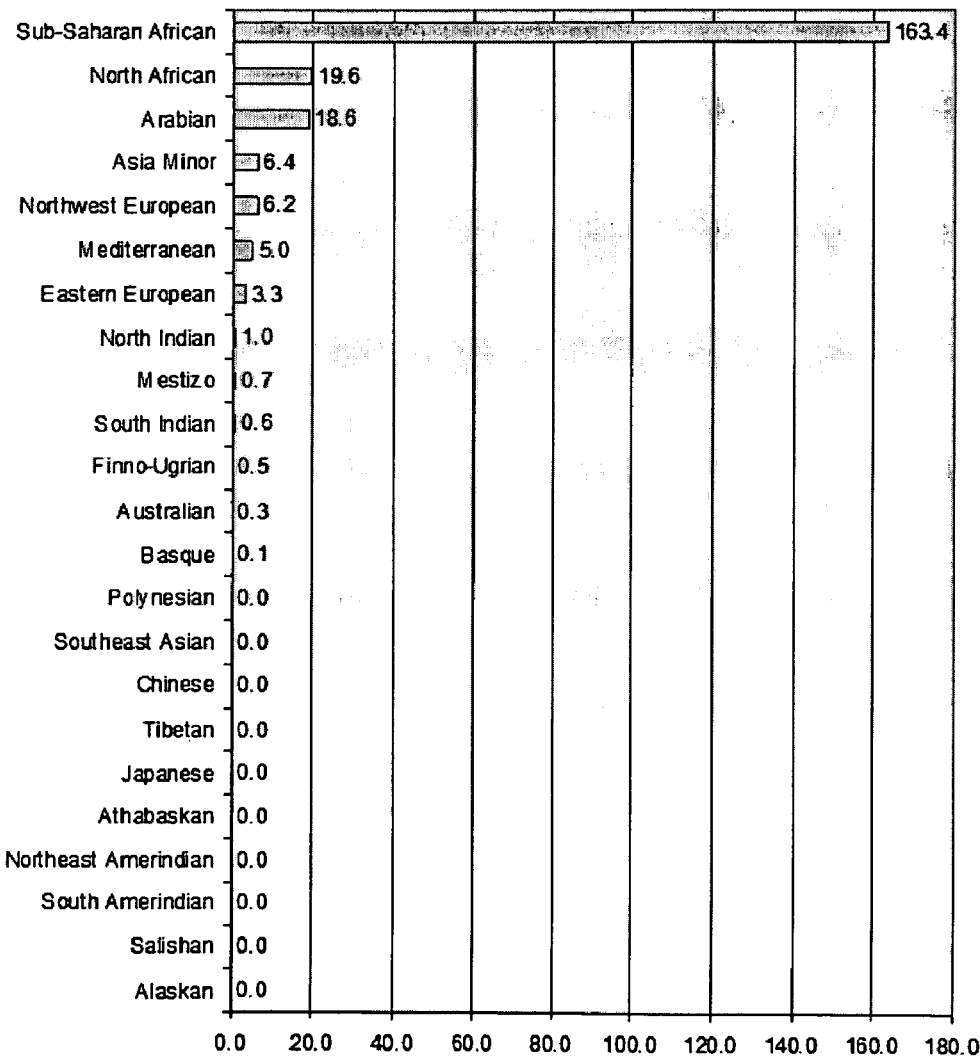

FIG. 27

| Locus | Allele 1 | Allele 2 |
|---|---|---|
| Amel | X | X |
| D3S1358 | 16 | 16 |
| TH01 | 6 | 9.3 |
| D21S11 | 29 | 30.2 |
| D18S51 | 15 | 16 |
| D5S818 | 11 | 13 |
| D13S317 | 12 | 13 |
| D7S820 | 9 | 10 |
| D16S539 | 10 | 11 |
| CSF1PO | 10 | 11 |
| vWA | 18 | 19 |
| D8S1179 | 12 | 13 |
| TPOX | 8 | 11 |
| FGA | 22 | 23 |

FIG. 30
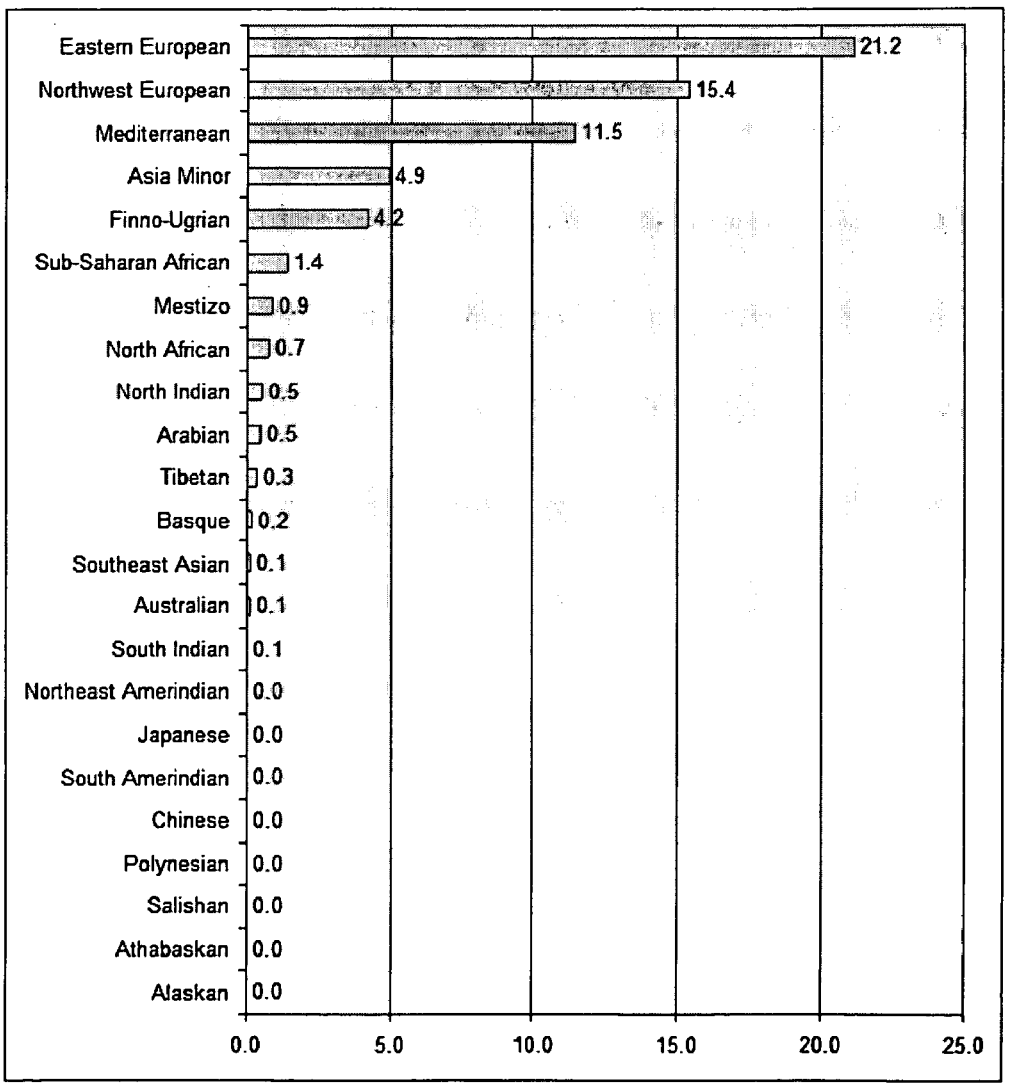

FIG. 31

| Locus | Allele 1 | Allele 2 |
|---|---|---|
| Amel | X | Y |
| D3S1358 | 15 | 16 |
| TH01 | 7 | 9 |
| D21S11 | 29 | 30 |
| D18S51 | 13 | 14 |
| Penta E | 5 | 15 |
| D5S818 | 11 | 12 |
| D13S317 | 8 | 11 |
| D7S820 | 10 | 11 |
| D16S539 | 9 | 11 |
| CSF1PO | 10 | 12 |
| Penta D | 9 | 12 |
| vWA | 14 | 17 |
| D8S1179 | 13 | 14 |
| TPOX | 8 | 11 |
| FGA | 23 | 24 |
| D2S1338 | 18 | 23 |
| D19S433 | 13 | 14 |
| F13A1 | 3.2 | 6 |
| F13B | 9 | 10 |
| FES/FPS | 11 | 12 |
| LPL | 10 | 12 |

FIG. 32
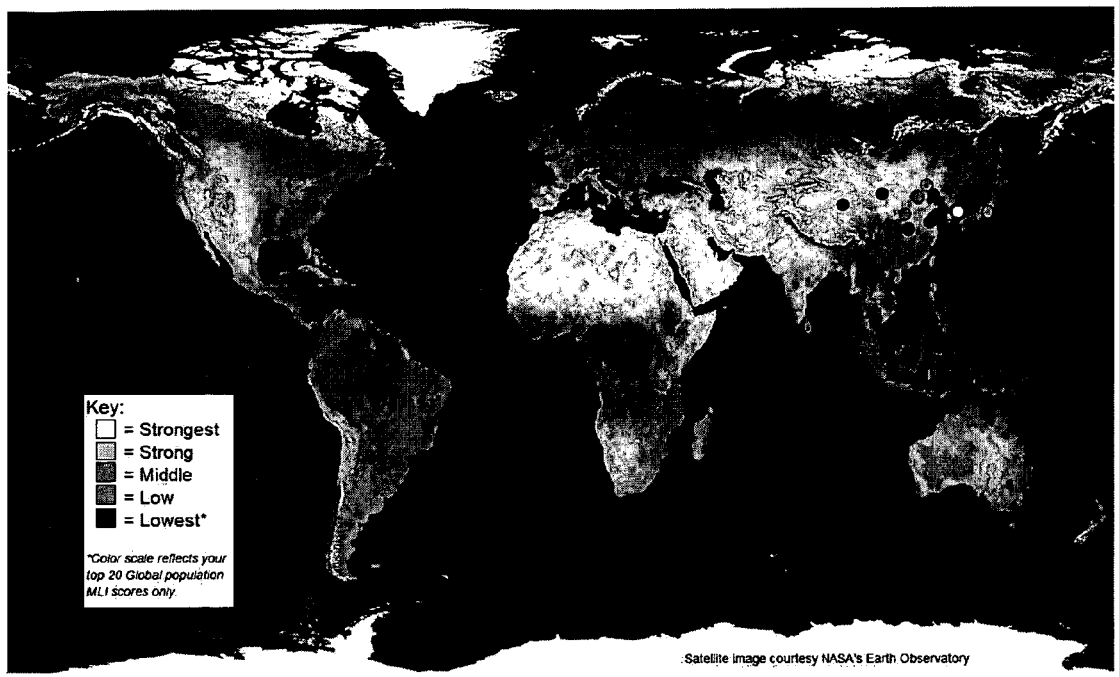
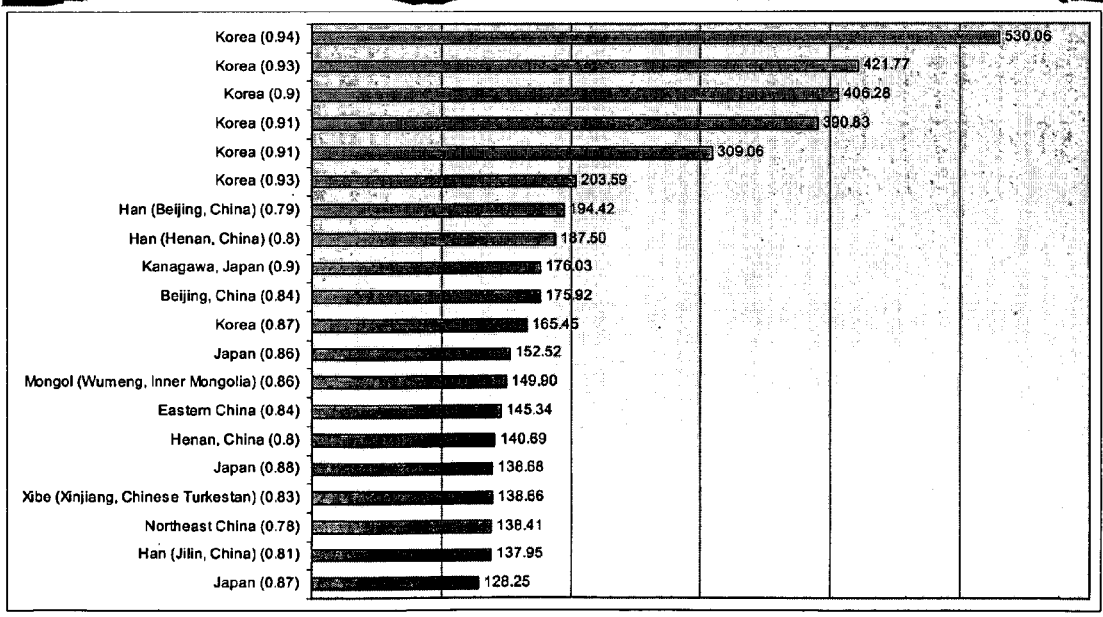

FIG. 33
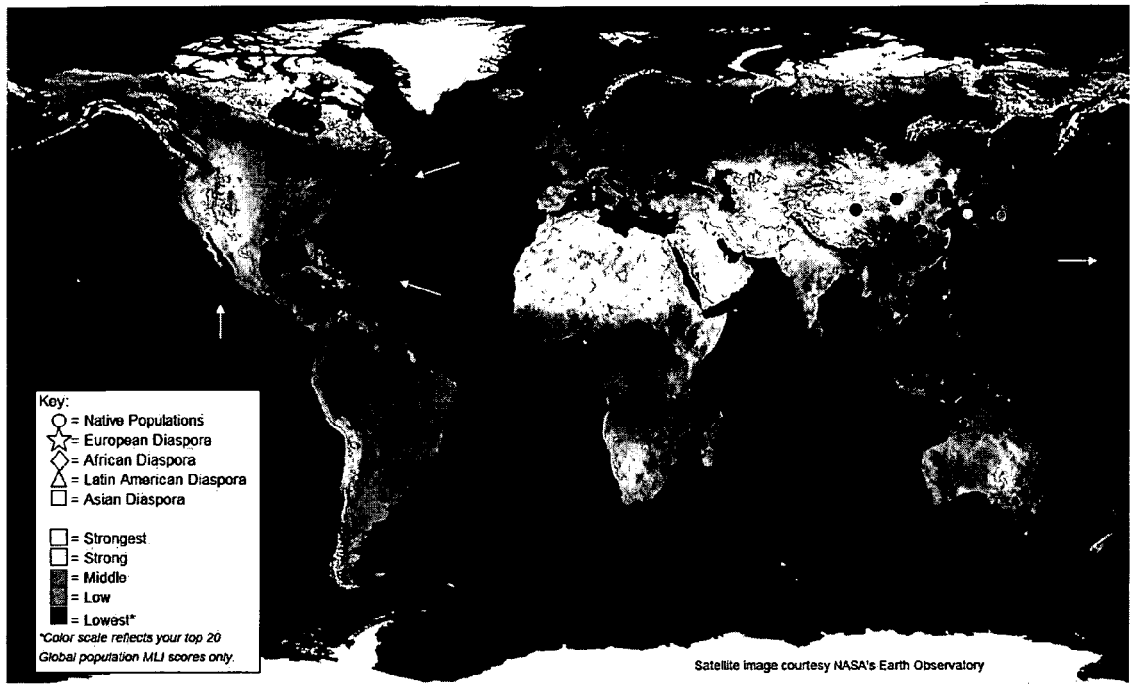
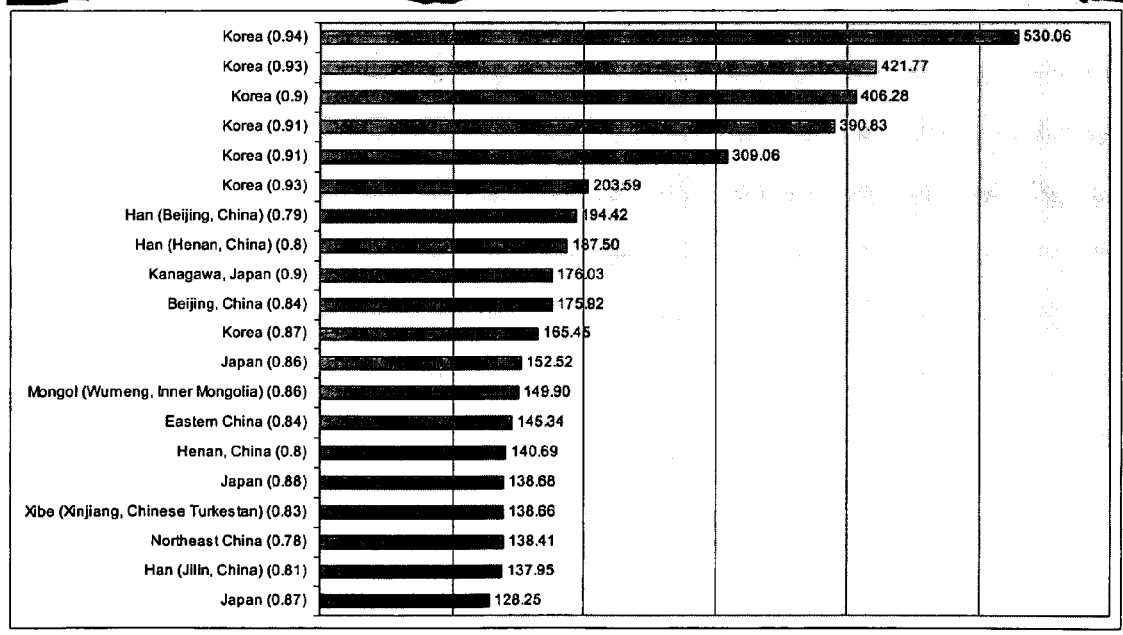

FIG. 34
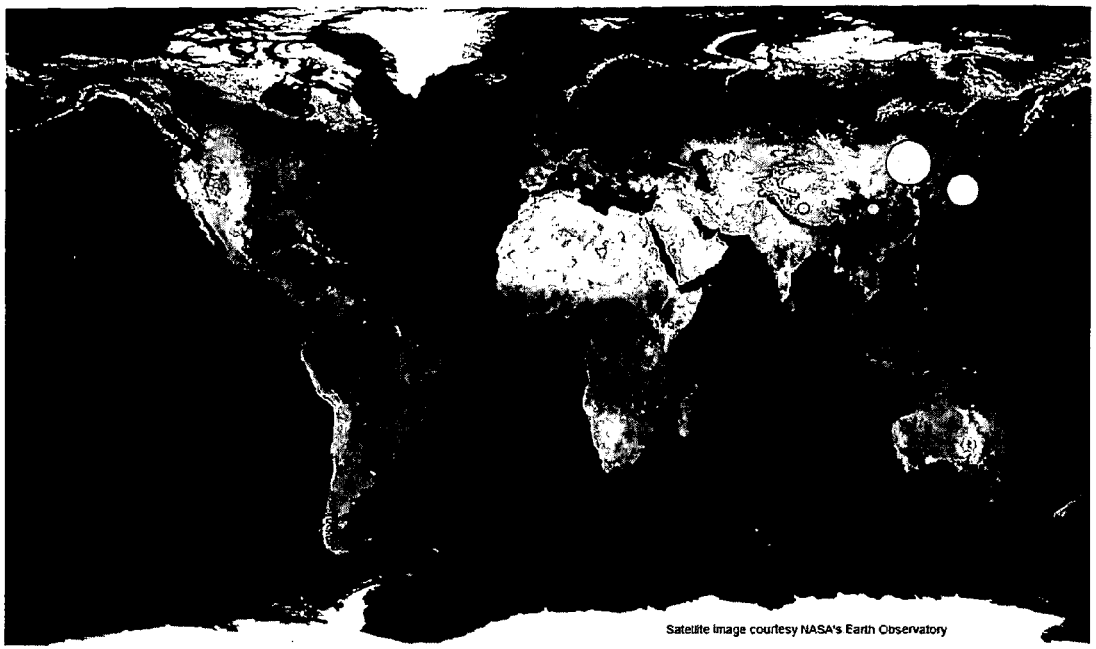
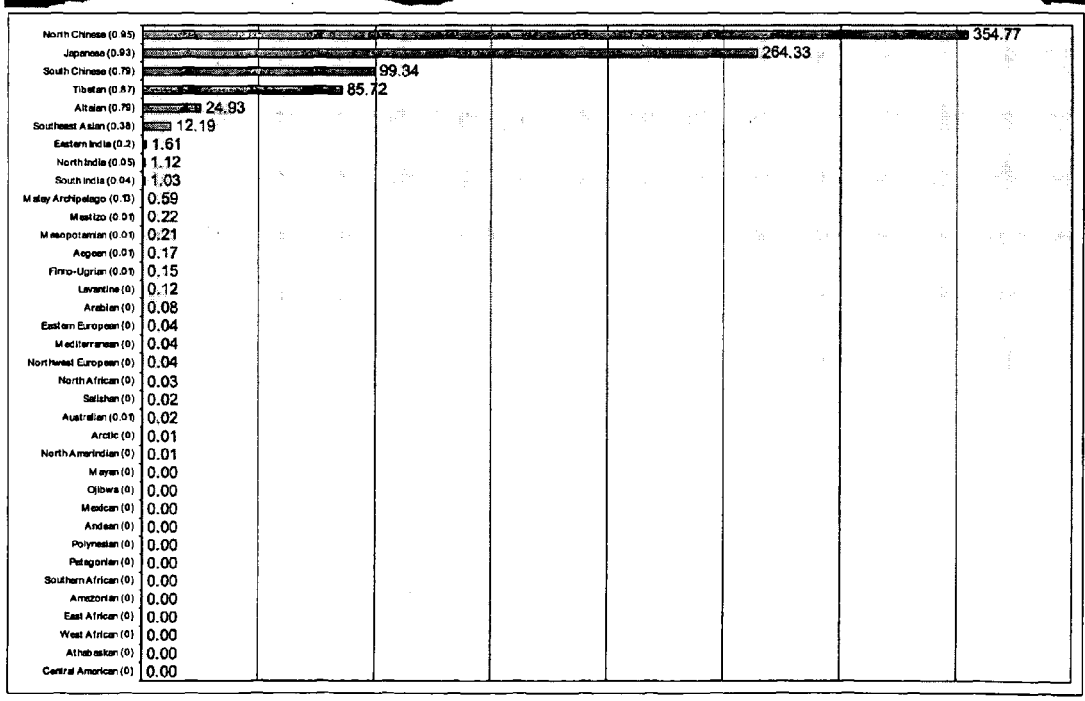

FIG. 35

| Locus | Allele 1 | Allele 2 |
|---|---|---|
| Amel | X | Y |
| D3S1358 | 15 | 16 |
| TH01 | 7 | 9 |
| D21S11 | 29 | 30 |
| D18S51 | 14 | 15 |
| Penta E | 11 | 12 |
| D5S818 | 10 | 11 |
| D13S317 | 8 | 11 |
| D7S820 | 8 | 11 |
| D16S539 | 10 | 11 |
| CSF1PO | 11 | 12 |
| Penta D | 9 | 12 |
| vWA | 14 | 17 |
| D8S1179 | 13 | 14 |
| TPOX | 8 | 11 |
| FGA | 21 | 22 |
| D2S1338 | 19 | 24 |
| D19S433 | 13 | 15.2 |
| F13A1 | 5 | 6 |
| F13B | 9 | 10 |
| FES/FPS | 11 | 12 |
| LPL | 10 | 12 |

FIG. 36
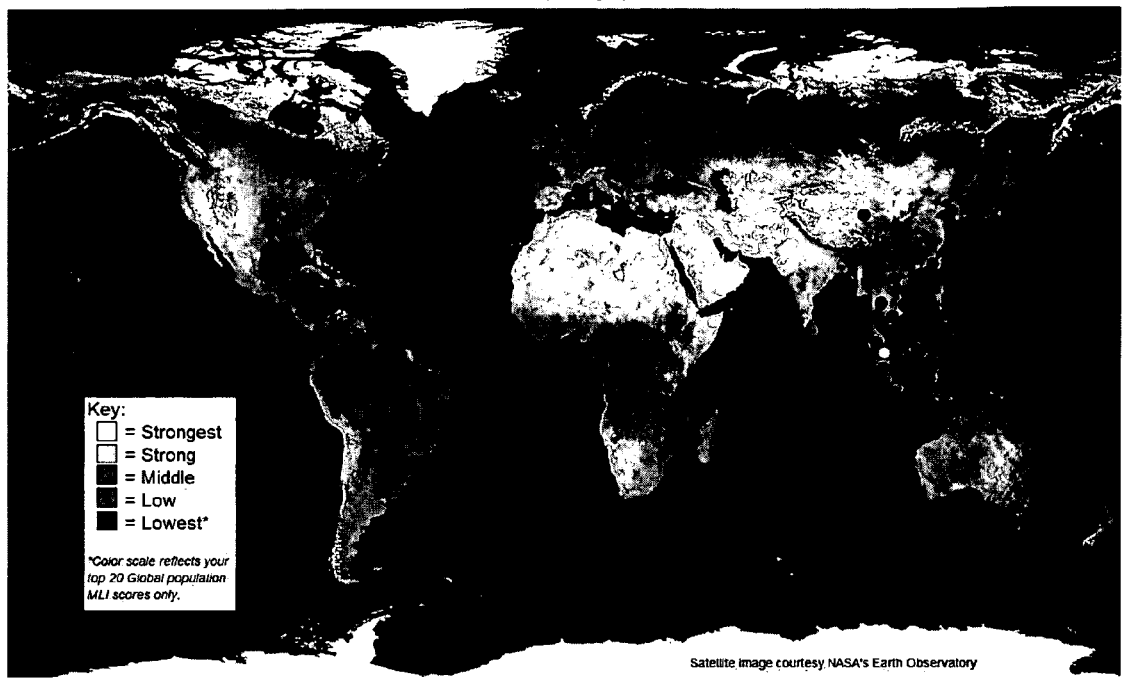
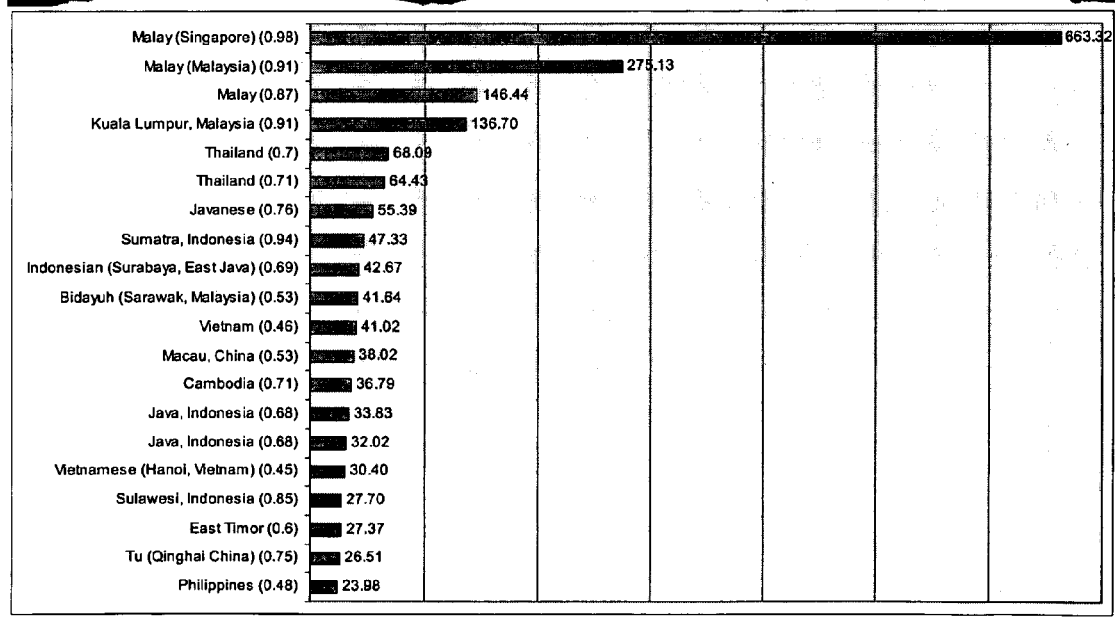

METHODS OF DETERMINING RELATIVE GENETIC LIKELIHOODS OF AN INDIVIDUAL MATCHING A POPULATION

RELATED APPLICATION

This patent application is a continuation-in-part of U.S. patent application Ser. No. 11/621,646 filed on Jan. 10, 2007 now abandoned, which claims the benefit of priority to U.S. Provisional Patent Application No. 60/766,426 filed on Jan. 18, 2006, entitled "GeoGenetic Profile," both of which are hereby incorporated by reference in their entireties, including all text and figures.

FIELD

Exemplary embodiments of the present invention are generally directed to methods of determining an individual's relative likelihood of having a genetic match with one or more local populations, as compared to a generic index population, (herein referred to as a Match Likelihood Index or MLI). The individual may be a human or any other organism.

Further example embodiments include methods that include comparing an individual's MLI for a given population to MLI scores simulated for members of that population. Other embodiments include methods that include comparing an individual's MLI for a given population to MLI scores for a group of actual members of that population.

Methods of the invention may be used for example to identify an individual person's most likely geographic origin or the most likely geographic origin of an individual's ancestors. Such uses may be desirable for example with respect to law enforcement or for genealogy purposes. These methods may also be used to determine the likely geographic origin of a particular animal, species of animal etc. Populations are not necessarily geographic in nature. Thus, methods may also be used to identify the breed, species, kingdom, etc. of an organism. For example, the methods may be used to identify the particular species of dog or horse, e.g., for breeding, selling, or showing purposes.

Also encompassed are systems, apparatuses, kits, and machine-readable medium relating to such methods.

BACKGROUND

For decades, scientists have known that geographical genetic diversity exists. People around the world share genetic traits with their neighbors that distinguish them from peoples living further away.

Traditional anthropology has classified four races corresponding to four major continents: African, European, Asian and American. This simple system of classification dates back to the $18^{th}$ century taxonomist Carolus Linnaeus and is still commonly used when describing ethnic groups and individuals. Certain areas of each continent are traditionally designated as pure representatives of each race, and other regions are assumed to be mixed between these presumably unmixed areas.

Early applications of genetic science used the traditional racial scheme in a "hand-me-down" fashion. The genetic differences between peoples traditionally identified as Black, White, Asian and American Indian in North America are great enough to allow a rough estimate of an individual's "percentage" membership in each racial group. This approach has been used for medical and police applications as well as for individuals interested in learning more about their genetic ancestry. However, this racial scheme creates problems when used outside of the core regions ancestral to modern North Americans. Mankind cannot be described by a handful of 3-5 simplistic racial categories. Simplistic divisions of the world into 3-5 continents ignores important unique regions that do not neatly fall into presumed racial categories, such as North Africa, Polynesia or India.

For instance, a Pakistani or Samoan can be classified as some percentage of American Indian, European, East Asian and Sub-Saharan Africa, but the resulting classification would be meaningless. At a theoretical level, this approach adds nothing to the popular or scientific understanding of human relationships and bestows an air of scientific legitimacy to outdated ideas of race. At a practical level, these theoretical limitations might have harmful consequences for example, for an individual administered a drug regimen based on a misleading percentage calculation. Clearly, the four-fold racial division provides an incomplete and misleading portrayal of the diversity of the human species.

Other genetic tests to determine ancestry include Y chromosome and mtDNA tests. However, while each person has thousands of ancestors, Y chromosome or mtDNA tests can only provide information about one lineage a person has inherited from one direct lineal ancestor.

SUMMARY

The present inventors have invented methods of describing the genetic landscape of mankind by describing the world not as a stark checkerboard of racial divisions, but as a rich tapestry of overlapping world regions. The present methods objectively identify groups of populations based on neutral genetic markers. The result is a network of populations, such as world regions, each characterized by shared history and genetic patterns. Geographical outlines of these regions echo borders of countless empires, trade networks and kin groups.

As described further herein, the statistical methods developed and used by the present inventors, may be used for purposes other than identifying an individual's most likely ancestral geographic origin(s). By way of non-limiting example, methods, apparatuses, systems, machine readable medium, and kits may be adapted for uses such as identifying most likely geographic origin(s) of an individual person or animal (e.g., for law enforcement purposes); or for identifying a most likely breed(s) or species of animal.

Exemplary embodiments are generally directed to methods of determining an individual's relative likelihood of having a genetic match with one or more local populations, as compared to a generic index population. In particular, such methods may include determining a likelihood of the individual belonging to the at least one local population, e.g., by comparing genetic markers of the individual to the frequency of such markers occurring in at least one local population; determining a likelihood of the individual belonging to a generic index population, e.g., by comparing genetic markers of the individual to the frequency of such markers occurring in a generic index population; and comparing the likelihoods to determine the individual's relative likelihood of having a genetic match with the one or more local populations. The relative likelihoods with respect to each of several local populations may be ranked, if desired, to further demonstrate the likelihood of the individual matching each local population.

Further example embodiments include methods that include comparing (1) an individual's relative likelihood of having a genetic match with a given population, as compared to a generic index population for a given population (an individual's MLI score for a given population) to (2) relative likelihoods of simulated members of the given population, as compared to a generic index population for a given population (MLI scores simulated for members of the population). Other example embodiments include methods that include comparing (1) an individual's relative likelihood of having a genetic match with a given population, as compared to a generic index population for a given population (an individual's MLI score for a given population) to (2) relative likelihoods of actual members of the given population, as compared to a generic index population for a given population (actual MLI scores for members of the population).

Example embodiments are also directed to apparatuses that include a server and software capable of performing methods herein or a portion thereof, such as determining a relative likelihood of an individual belonging to a local population as compared to a generic index population, or for comparing an individual's MLI score for a given population to MLI scores for members of that population (simulated or actual). Example embodiments are also directed to systems that include a server coupled to a database, where the database includes information regarding genetic markers occurring in at least one local population and/or in a generic index population.

Example embodiments are also directed to kits that include at least one device for determining genetic markers of an individual and a computer readable program product that includes a computer readable medium and a program capable of determining a relative likelihood of an individual belonging to a local population as compared to a generic index population and/or for comparing an individual's MLI score for a given population to MLI scores for members of that population, where the members of the population may be simulated or actual members.

Example embodiments are also generally directed to machine readable medium that include code segments or programs embodied on a medium that cause a machine to perform the present methods or any portion thereof.

BRIEF DESCRIPTION OF THE DRAWINGS

Embodiments of the invention are herein described, by way of non-limiting example, with reference to the following accompanying drawings:

FIG. 6 is an illustration of a composition of individual ethnic and national American Indian populations as determined by example methods;

FIG. 7 is an illustration of a composition of individual ethnic and national European and Near Eastern populations as determined by example methods;

FIG. 8 is an illustration of a composition of individual ethnic and national Sub-Saharan African and Central and South Asian populations as determined by example methods;

FIG. 9 is an illustration of a composition of individual ethnic and national East Asian and Pacific populations as determined by example methods;

FIG. 11 is a table listing characteristic World Region scores by percentile for Caucasians living in the United States;

FIG. 12 is a table listing characteristic Europa Sub-Region scores by percentile for Caucasians living in the United States;

FIG. 13 is a table listing characteristic World Region scores by percentile for African Americans living in the United States;

FIG. 14 is a table listing characteristic World Region scores by percentile for Hispanics living in the United States;

FIG. 15 depicts an example distribution of frequencies for a subset of a global population database at an example allele D8S1179 in accordance with example embodiments;

FIG. 16 depicts a sample individual genetic profile where genetic markers were determined at 13 alleles in accordance with example embodiments;

FIG. 17 is an illustration an example of partial matching results for a Basque individual, where the ten most likely matching populations, are ranked in order with the most likely matching population at the top;

FIG. 18 is a numerical illustration and FIG. 19 shows a relative numerical illustration on a world map;

FIG. 20 is a numerical illustration and FIG. 21 shows a relative numerical illustration on a world map;

FIG. 23 depicts a genetic profile of an African individual, setting forth allele values at each of 13 loci in accordance with an example embodiment;

FIG. 25 is an illustration (both numerically and on a world map) of the top twenty Global population matches for the individual of FIG. 23 after performing a Global Population Match in accordance with example methods;

FIG. 26 is an illustration (both numerically and on a world map) of the top twenty high resolution World Region matches for the individual of FIG. 23 after performing a World Region match in accordance with example methods;

FIG. 27 depicts a genetic profile of a European individual, setting forth allele values at each of 13 loci in accordance with an example embodiment;

FIG. 30 is an illustration (both numerically and on a world map) of the top twenty high resolution World Region matches for the individual of FIG. 27 after performing a World Region match in accordance with example methods;

FIG. 31 depicts a genetic profile of a Korean individual, setting forth allele values at each of 21 loci in accordance with an example embodiment;

FIG. 32 is an illustration (both numerically and on a world map) of the top twenty Native population matches for the individual of FIG. 31 after performing a Native Population Match in accordance with example methods;

FIG. 33 is an illustration (both numerically and on a world map) of the top twenty Global Population matches for the individual of FIG. 31 after performing a Global Population Match in accordance with example methods;

FIG. 34 is an illustration (both numerically and on a world map) of the top high resolution World Region matches for the individual of FIG. 31 after performing a World Region match in accordance with example methods;

FIG. 35 depicts a genetic profile of a Malay (Singapore) individual, setting forth allele values at each of 21 loci in accordance with an example embodiment;

FIG. 36 is an illustration (both numerically and on a world map) of the top twenty Native population matches for the individual of FIG. 35 after performing a Native Population Match in accordance with example methods;

DETAILED DESCRIPTION

Figure 1:
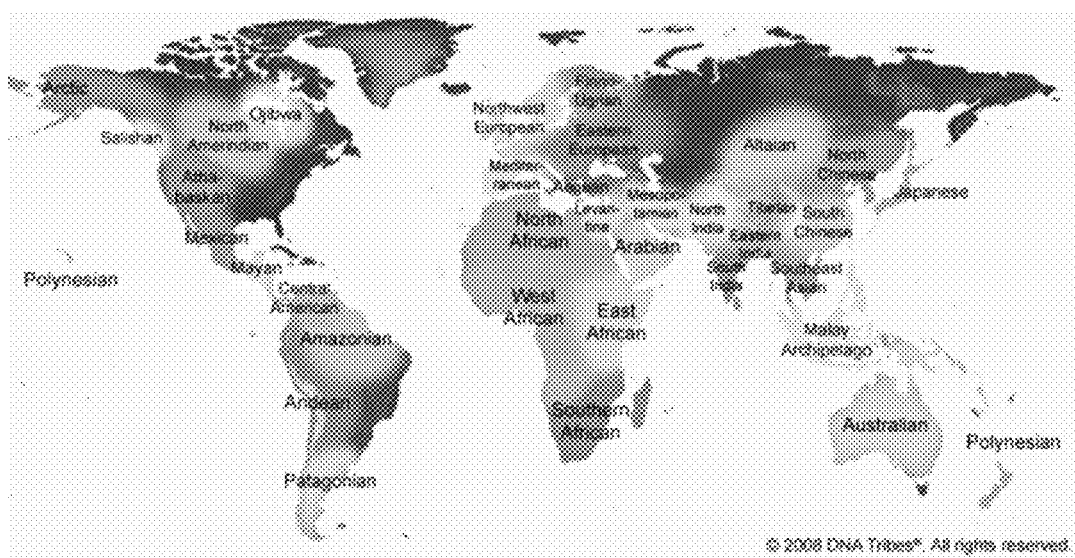
FIG. 1 illustrates approximate geographical boundaries of illustrative World Regions according to example embodiments.

The aspects, advantages and/or other features of example embodiments of the invention will become apparent in view of the following detailed description, which discloses various non-limiting embodiments of the invention. In describing example embodiments, specific terminology is employed for the sake of clarity. However, the embodiments are not intended to be limited to this specific terminology. It is to be understood that each specific element includes all technical equivalents that operate in a similar manner to accomplish a similar purpose.

It should be understood that example methods, apparatuses, systems, kits, and machine readable medium described herein may be adapted for many different purposes and are not intended to be limited to the specific example purposes set forth herein.

As used herein, "a" or "an" may mean one or more. As used herein, "another" may mean at least a second or more.

The terms "individual" and "organism" are used interchangeably herein and are intended to encompass an individual animal, including e.g., mammals (such as humans, dogs, horses, cats, etc.), and non-mammals. As used herein, the term "individual" is not limited to humans.

The term "population" is intended to encompass a grouping of more than one individual or organism. A "local population" is a grouping or subset of a larger population ("generic index population") of individuals or organisms. A "local population" may, but does not necessarily, include a group of individuals from a similar geographic location (which may be referred to herein as a "World Region" or "World Region population"). Other "local populations" may include non-geographic groupings, such as groupings at a cladistic level. Non-limiting examples of "local populations" may include for example, towns, nations, ethnic groups, continents, species, subspecies, genus, family, order, class, phylum, or other grouping of individuals.

A "generic index population" is a grouping of more than one local population, which may be used for example, as a scaling population to which local population information is compared. By way of non-limiting example, a local population may be a nation within a generic index population of the world, or other geographic subsets and larger populations such as region/world, town or village/nation, nation/continent, etc. Local or generic populations may have boundaries that do not match nation or continent boundaries. Alternatively, the local to generic relationship may not be related to geography, such as a local population of a breed within a generic index population of a species, subspecies/species, species/genus, genus/family, family/kingdom, etc. Data regarding a "generic index population" may include for example an average, median or other formulation of data from all of the local populations making up the generic index population.

The term "genetic marker" is intended to encompass any portion of an individual's (organism's) genome that may be identified and compared to similar portions of the genome of a population of individuals. By way of non-limiting example, genetic markers may include a marker at any suitable genetic loci, such as allele values in the DNA at particular autosomal loci, or other genetic markers. Thus, genetic markers in an individual may be determined by sequencing the individual's allele values from a sample of the individual's DNA at N autosomal loci, where N is any positive integer. Standard forensic markers often used for paternity/maternity and other forensic DNA testing may be useful genetic markers for the present methods. Non-limiting examples of possible markers that may be used, include but are not limited to D3S1358, TH01, D21S11, D18S51, Penta E, D5S818, D13S317, D7S820, D16S539, CSF1PO, PentaD, vWA, D8S1179, TPOX, FGA, D2S1338, D19S433, F13A1, F13B, FES/FPS, and LPL.

The determination of how many and which allele values and which loci are selected may vary depending many factors. For example, such factors may include what information is being sought, the availability of data with respect to a population to which the individual may be compared, and information regarding the uniqueness of allele values at particular loci. By way of non-limiting example, allele values may be sequenced at one or more short tandem repeat (STR) loci or single nucleotide polymorphism (SNP) loci. According to example embodiments allele values may be sequenced at at least 9 STR or SNP loci, or at least 13 STR or SNP loci, or at least 21 STR or SNP loci. STR loci are presently among the most informative polymorphic markers in the genome, but the invention is not intended to be limited in any way to markers at autosomal STR loci.

The term "match" as used herein is not intended to denote an exact match, but rather an indication of the most likely genetic match between an individual and a population, based on statistical methods. For example, an individual may be designated herein as matching a population based on their relative likelihood of matching that population (as compared to a generic index population) being greater than the relative likelihood of "matching" one or more other populations. A match with a particular ethnic or national population sample does not guarantee that the individual or a recent ancestor (parent or grandparent, for instance) are a member of that population (e.g., ethnic group). However, a match may indicate for example, a population where the individual's combination of ancestry is common, which is most often due to shared ancestry with that population.

Example embodiments are generally directed to methods of determining an individual's (including mammals such as humans, or other animals) relative likelihood of having a genetic match with one or more local populations, as compared to a generic index population. In particular, examples of such methods may include determining a genetic likelihood of the individual belonging to at least one local population (e.g., by comparing genetic markers of the organism to the frequency of such markers occurring in at least one local population); determining a genetic likelihood of the individual belonging to a generic index population (e.g., by comparing genetic markers of the organism to the frequency of such markers occurring in a generic index population); and comparing the likelihood of the individual belonging to the at least one local population to the likelihood of the individual belonging to the generic index population to determine the individual's relative likelihood of a genetic match with the one or more local populations.

According to example embodiments, methods of the invention may be used to identify the most likely geographic origin of an individual's ancestors. Such uses may be desirable for example for genealogy purposes. Thus, the likelihood of an individual human belonging to (e.g., having ancestors from) one geographic local population (also referred to as a "World Region") may be calculated and compared to the likelihood of that individual belonging to a generic world index population that includes a plurality of geographical local populations.

The methods herein may also be used for purposes other than identifying an individual's most likely ancestral geographic origin(s). For example, in addition to identifying an individual's most likely ancestral geographic origin(s), methods, apparatuses, systems, machine readable medium, and kits may be adapted for uses such as: identifying most likely geographic origin(s) of an individual themselves; identifying most likely geographic origin(s) of an animal; and identifying most likely breed(s) or species of animal. These uses are non-limiting examples of some of the many possible embodiments.

According to example embodiments, methods of the invention may be used to identify an individual's most likely geographic origin. Such uses may be desirable for law enforcement purposes. For example, if a DNA sample is left behind at a crime scene, it may be possible to determine information about the most likely national/regional origins of the individual whose DNA was at the crime scene and analyzed.

As indicated above, other example methods may be used to identify a breed, species, kingdom, etc. of an organism. By way of non-limiting example, methods may be used to identify the particular breed of dog or horse, which may be useful e.g., for breeding, selling, and/or showing purposes. Thus, example embodiments may include calculating the relative likelihood of an individual animal (such as a dog or horse) belonging to one breed as compared to the likelihood of that animal belonging to an index population of the species. Other example embodiments, involving non-humans, may include using the methods herein to determine a likely geographic origin of a particular animal (or its ancestors), species of animal, etc.

Example embodiments include determining a genetic likelihood of an individual belonging to at least one local population. Example methods of determining the likelihood of an individual belonging to at least one local population may include comparing one or more genetic markers present in the individual (e.g., at a plurality of genetic loci) to the frequency of such genetic markers occurring in the at least one local population. Genetic markers in the individual may be determined for example, by sequencing the individual's allele values from a sample of the individual's DNA at N autosomal loci, wherein N is any positive integer. The autosomal loci may be for example, STR loci or SNP loci, but are not limited to such.

The likelihood of the individual belonging to at least one local population may be determined for example, by a method that includes extracting from a database, frequencies p matching the individual's allele value at each locus w, w=1 ... 2N, where N is the number of genetic loci for which data is collected from the individual, for each local population; and determining a joint probability $P_j$ of an individual matching a local population j by multiplying the extracted frequencies $p_{w|j}$ using the following formula $$P_j = \prod_{w=1}^{2N} p_{w|j}$$

According to example embodiments, the joint probability $P_j$ may be adjusted for confidence. By way of non-limiting example, the joint probability $P_j$ of an individual matching a local population j, may be adjusted by determining a lower bound of a confidence interval to arrive at a joint matching probability $\tilde{P}_j$ (also referred to herein as match likelihood or likelihood). $\tilde{P}_j$ may be determined for example by a method using the following formula:

$$\tilde{P}_j = \exp\left\{\log P_j - Z_C \sqrt{\frac{1}{n_j} \sum_{w=1}^{2N} \frac{1 - p_{w|j}}{p_{w|j}}}\right\}$$

wherein $p_{w|j}$ is a frequency of the individual's allele value at each locus w in population j, w=1 ... 2N, where N is the number of genetic loci for which data are collected from the individual, $n_j$ is the number of individuals in population j for which genetic data were collected, and $Z_C$ is a z-score corresponding to the C confidence level.

According to example embodiments, a local population may be defined by a method that includes using any multivariate clustering algorithm (such as K-means) to divide data from a set of population samples into groups. For example, the larger database of populations may be separated into K groups. Genetic marker (e.g., allele) frequencies for a World Region K can be for example, a median, mean or any other general combination of genetic marker frequencies of local populations in group K. This local World Region population may be compared to a generic index population as described further below. By way of non-limiting example, representative populations for World Regions may be obtained using a K-means analysis of all populations in a global database. This analysis may identify major divisions in global genetic variation corresponding to major continental regions (e.g., European and Near Eastern, Sub-Saharan African, East Asian and Central and South Asian, Native Central and South American, Pacific, and American Indian). Representative populations for each of these World Regions may be chosen by their proximity to cluster centers. These representatives are used as reference points for the clusters, to which individuals are compared to estimate their continental ancestry. According to example embodiments, World Regions may be determined by median, means or other statistical methods.

Thus, various local populations (such as World Regions) may be identified by objective mathematical criteria and information regarding such populations may be maintained in a database to be used for determining an individual's most likely genetic matches to such populations. According to example embodiments many of these World Regions may correspond to cultural or linguistic groups. For instance, Slavic-speaking peoples share a predominance of the Eastern European region. Other World Regions cross national and cultural boundaries as they exist today. For instance, the Asia Minor region can be found from modern day Southern Italy to Turkey to Afghanistan, and includes speakers of Indo-European, Afro-Semitic, Altaic and Indo-Iranian languages.

According to example embodiments, there may be occasions where one or more of an individual's allele values are not used in calculating matches. In particular, there exist numerous allele values at each particular locus Z, which are not informative when calculating matches. Let $p_j$ denote the proportion of individuals having specific allele value z in population j. An allele "z" may be identified as a "weak allele," and therefore according to certain embodiments may not be used in the calculations and methods herein, if it fails certain mathematical criteria. By way of non-limiting example, a particular weak allele may not be used in the calculations herein if the allele fails both of the following criteria:

a) $p_{max}/p_g < 3$, where $p_{max}$ is the maximum frequency observed in all populations at allele z of locus Z and $p_{95}$ is the 95% percentile value of the frequencies.

b) at least 90% of the top 20 populations with the highest $p_j$ values are in at most two World Regions.

An example of a weak allele, that is, an allele failing both criteria is provided below. It should be noted that the exact criteria used to define a weak allele, may vary within the scope of these embodiments.

According to example embodiments, when a particular allele occurs in an individual, but is not observed in a population sample, a very low allele frequency (such as 0.001) may be imputed, so as to err on the side of over-exclusiveness. This is in contrast to methods used in standard paternity match analysis and other forensic identity analysis methods, where match calculations aim to err on the side of over-inclusiveness. For example, in other methods, when a particular allele is not observed in a population, a minimum value is typically imputed according to a standard formula, so that a frequency of zero is not used in calculations.

Example embodiments of the methods herein include determining a genetic likelihood of an individual belonging to a generic index population. Example methods of determining the likelihood of an individual belonging to a generic index population may include comparing one or more genetic markers present in the individual (e.g., at a plurality of genetic loci) to the frequency of such genetic markers occurring in the generic index population.

According to example embodiments, the likelihood of the individual belonging to a generic index population may be determined by a method that includes extracting from a database, frequencies p matching the individual's allele value at each locus w, w=1 ... 2N, where N is the number of genetic loci for which data is collected from the individual, for the generic index population GI (also referred to herein as a generic human index or GHI in the case where the individual is a human); and determining a joint probability $P_{GI}$ of an individual matching the generic index population by multiplying the extracted frequencies $p_{w|GI}$ using the following formula $$P_{GI} = \prod_{w=1}^{2N} p_{w|GI}.$$

According to example embodiments, the joint probability $P_{GI}$ may be adjusted for confidence. By way of non-limiting example, the joint probability $P_{GI}$ of an individual matching a generic index population may be adjusted by determining a lower bound of a confidence interval to arrive at a joint matching probability $\tilde{P}_{GI}$. $\tilde{P}_{GI}$ may be determined for example by a method using the following formula:

$$\tilde{P}_{GI} = \exp\left\{\log P_{GI} - Z_C \sqrt{\frac{1}{n_{GI}} \sum_{w=1}^{2N} \frac{1 - p_{w|GI}}{p_{w|GI}}}\right\}$$

$P_{GI}$ is the joint probability of an individual matching the generic index population, $p_{w|GI}$ is a frequency of matching the individual's allele value at each locus w, w=1 ... 2N, and N is the number of genetic loci for which data is collected from the individual. $n_{GI}$ may be determined by the following formula:

$$n_{GI} = \frac{1}{K} \sum_{j=1}^{K} n_j$$

where K is a number of local populations used to calculate the generic index population, and $n_j$ is a number of individuals comprising local population j.

The frequency of genetic markers occurring in a generic index population may be determined for example, by determining frequencies of alleles occurring at each of N loci for multiple local populations and averaging or determining the median of frequencies for each allele for all of the multiple local populations. According to non-limiting example embodiments, the local population may be a World Region population and the generic index population is an average or median of all World Region populations.

As indicated above, a local population may be a nation within a generic index population of the world, or other geographic subsets and larger populations such as region/world, town or village/nation, nation/continent, etc. Local or generic populations may have boundaries that do not match nation or continent boundaries. Alternatively, the local to generic relationship may not be related to geography, such as a local population of a breed within a generic index population of a species, subspecies/species, species/genus, genus/family, family/kingdom, etc. For example, a generic index population may be selected from the group consisting of a kingdom, phylum, class, order, family, genus, species, and any subdivisions thereof. Thus, by way of example, each local population may be a breed of organisms, and the generic index population may be a species of organisms. Further, the individual may be an individual dog, where each local population is a breed of dogs, and the generic index population is dogs.

The GI (or GHI) is a fixed reference point to which all individual matches with actual populations are measured and serves as the "null hypothesis" for each match that the individual's genetic profile is "generic" rather than indicative of e.g., regional or ethnic genetic affiliation. As more data becomes available for one or more local populations making up the global index population, for example if a new set of data is obtained for a new native tribe or individual data is added to known local populations, the GI data may be recalculated. When this occurs, methods herein may be repeated to provide updated likelihood calculations.

Example embodiments may further include comparing the likelihood of the individual belonging to at least one local population to the likelihood of the individual belonging to a generic index population. The methods of comparison may include for example, comparing joint probabilities or joint matching probabilities (adjusted for confidence). Methods of calculating the joint probabilities, whether or not the probabilities are adjusted for confidence, and/or how they are adjusted may vary within the scope of the present methods.

Example embodiments of such comparisons may include dividing the likelihood of the individual belonging to a first local population by the likelihood of the individual belonging to a generic index population to determine a relative likelihood ratio of the individual belonging to the local population. It is contemplated that methods within the scope of this application of comparing the probability of an individual matching a local population to the probability of that individual matching a generic index population, may include methods other than pure division.

According to example embodiments, a relative likelihood ratio LR (or match likelihood index (MLI) score) of an individual belonging to a local population as compared to a generic population may calculated using the following formula:

$$LR = \tilde{P}_j / \tilde{P}_{GI},$$

wherein $\tilde{P}_j$ is a joint probability of an individual matching a local population j, adjusted for confidence; and $\tilde{P}_{GI}$ is a joint probability of an individual matching a global index population GI, adjusted for confidence.

Example embodiments may include comparing the likelihood of the individual belonging to a second or more local population(s) to the likelihood of the individual belonging to a generic index population to determine relative likelihood ratios of the individual belonging to each of the second or more local populations. Thus, several relative likelihood ratios may be obtained for each of several local populations. In such methods, the relative likelihood ratios of the individual belonging to each of several local populations may be ranked or otherwise denoted. Ranking or comparing more than one relative likelihood ratio may assist in demonstrating the likelihood of the individual matching each local population. For example, such rankings may include a numerical ranking with the local population having the highest relative likelihood ratio being first or last in a list. Such a list may include for example, the top ten or top twenty matching populations. Other methods of denoting the relative likelihood ratios may include color coding (e.g., on a map or on a chart of breeds); or any indication that would allow one (by sight, sound, feel (e.g., Braille), etc) to be able to determine which local population(s) are more likely a match to the individual than other local population(s).

According to other example embodiments, the relative likelihood ratios of the individual belonging to each of several local populations, may be numerically compared to one another. For instance, the most likely genetic matches may be presented for example with a match likelihood index (MLI) scores. For example, an MLI (or LR) score of 24.38 for Switzerland would indicate an individual's total combination of alleles is 24.38 times as common in Switzerland as in the world. MLI scores can be compared against each other as odds ratios. For instance, if an individual obtains an MLI score of 24.38 for Switzerland and an MLI score of 23.08 for Poland, this means that the individual's genetic profile is 24.38/23.08=1.05 times as likely to be Swiss as it is to be Polish. If the top ranked match MLI or LR for an individual is 30, and the second ranked match MLI is 15, one can divide 30/15 to see the relative likelihoods between those matches.

Matches may also include a TribeScore, listing an individual's MLI score's percentile in that population. TribeScores compare the individual's MLI scores to members of each ethnic group and world region. For instance, results listing "Switzerland (0.73)" (the TribeScore being indicated for example in parenthesis near each listed population.) would indicate that the MLI score is higher than 73% of scores from the Swiss reference population, and lower than 27% of these Swiss individuals. TribeScores between (0.25) and (0.75) are ordinary for a population. TribeScores provide additional context for each person's frequency-based MLI scores, by comparing an individual's MLI score for a given population to the MLI scores for (simulated or actual) members of that population.

An individual's TribeScore for population j can be computed for example using the following steps:

Step 1: Generate a distribution of MLI scores for population j using its observed allele frequencies as follows:

Let $p_{ik}$ denote the observed frequency of allele i on locus k in population j. Draw an allele value for each locus using these frequencies; such sampling process creates a single synthetic individual for population j. Use the k sampled allele values to produce and retain the MLI score. This score reflects the strength of the synthetic individual's match with population j. Repeat the sampling and MLI score computation for a large number N of synthetic individuals (N of at least 1,000). Denote the resulting MLI score distribution as $D_N$.

Alternatively, when actual individual DNA profiles from within a population are being used, rather than synthetic individuals, an MLI distribution may be calculated as follows:

For each individual DNA profile, an MLI score is calculated as described elsewhere in this application. This process of calculating MLI scores is repeated for all available individual DNA profiles until a distribution of scores $D_N$, is denoted.

Step 2: Compute an individual's MLI score for population j.

Use an individual's allele values to compute his/her MLI score for population k. Denote this score as $MLI_i$.

Step 3: Compute an individual's TribeScore.

An individual's TribeScore may be computed as the percentage of MLI scores in $D_N$ from Step 1 that are lower than $MLI_i$ computed in Step 2. This TribeScore may then be expressed as a percentile that measures how a person's MLI scores fit within the range of MLI scores observed within that population. Each TribeScore provides an empirical comparison of each person to each population. TribeScores in the range of (0.05) can be considered within the expected range for that population, and TribeScores below (0.05) indicate that ancestry from this population is unlikely.

Thus, example methods may include (a) determining an individual's relative likelihood of a genetic match with a local population as compared to a generic index population; (b) determining one or more additional individual's relative likelihood of having a genetic match with the local population as compared to the generic index population; and (c) comparing the individual's relative likelihood to the one or more additional individual's relative likelihood. According to example embodiments, the at least one additional individual may be at least one simulated individual. According to other embodiments, the at least one additional individual may include a group of actual individuals of the population.

According to example methods, determining an individual's relative likelihood of a genetic match with one or more local populations as compared to a generic index population (LR or MLI score) may include determining a genetic likelihood of the individual belonging to at least one local population; determining a genetic likelihood of the individual belonging to a generic index population; and comparing the likelihood of the individual belonging to the at least one local population to the likelihood of the individual belonging to the generic index population to determine the individual's relative likelihood of a genetic match with the one or more local populations (e.g., by division). Further, the genetic likelihood of the individual belonging to at least one local population, may be determined by comparing genetic markers present in the individual at a plurality of genetic loci, to the frequency of such genetic markers occurring in the at least one local population.

As with other embodiments discussed herein, the genetic likelihood of the individual belonging to a generic index population is determined by comparing genetic markers present in the individual at a plurality of genetic loci, to the frequency of such genetic markers occurring in the generic index population.

As discussed herein, the local population may be defined by a method comprising using a multivariate clustering algorithm by separating a local population database into K groups. The generic index population may be calculated e.g., as an average or median of all local populations in a database.

As explained above, determining at least one simulated individual's relative likelihood of having a genetic match with the local population as compared to the generic index population may include e.g., the steps of (a) denoting an observed frequency of allele i on locus k in population j; (b) drawing an allele value for each locus using the observed frequency to create a single synthetic individual for population j; and (c) using the k sampled allele values to produce and retain a simulated individual's relative likelihood score. The methods may further include repeating the process and determining individual relative likelihood scores for a large number N of synthetic individuals, and denoting the resulting score distribution as $D_N$.

According to example methods, comparing the individual's relative likelihood to the simulated individual's relative likelihood may include determining a percentage of likelihood. For example, where information is sought regarding an individual's most likely ethnic and geographical origin, a combination of methods, such as a Global Population Match, Native Population Match, World Region Match, and/or Europa match (described further herein), may present an ethnically and geographically specific indication of the individual's most likely origin. It should be noted that such Global, Native, World Region and Europa matches are non-limiting examples of some of the many possible methods that may be performed.

According to example embodiments, methods may include a Global Population Match to determine an individual's most likely genetic match to scores in $D_N$, that are lower than the individual's relative likelihood of a genetic match with a local population as compared to a generic index population.

In methods that include determining a relative likelihood for a group of actual individual members of a population having a genetic match with the local population as compared to the generic index population, the relative likelihood of the group of individual members of the group belonging to the generic index population may be calculated in accordance with methods described herein.

TribeScore can be used in conjunction with a ranked listing of frequency based MLI scores to express the range of populations in which a person's DNA profile fits. TribeScores can be used for any population where allele frequency data or individual population data are available, including genetic regions identified according to the procedures elsewhere in this document. As new population samples become available, MLI scores for individuals and for simulated individuals or groups of individuals may be updated and changed, and therefore the TribeScore may also be updated.

Multiple forms of analysis may be performed on an individual to determine possible matches to various local populations, including both native ethnic groups (discussed further below) and modern Diaspora and admixed populations. As used herein, the term "Global population" may include for example, all population samples in a database. The most likely genetic matches may then be presented for example by an MLI score for each. Such information regarding populations to which the individual most likely matches, whether expressed by MLI score or other measure of likelihood, may then be presented for example, to the individual. An example method of how such information may be presented may include plotting the locations of the Global populations that are the most likely matches on a map. Points and/or shading and/or coloring on the map to indicate locations of most likely matches may further include an indication of the magnitude of the likelihood of a match. For example, matches having the highest MLI score may be darkest, or a particular color, or scored in a certain manner, where a key may be provided to inform the reader of the meaning of whatever indication is provided.

Non-limiting examples of Modern Diaspora ethnic groups may include African-Americans, European-Americans or Asian-Americans. Modern Diaspora populations may be descended from immigrants who have recently moved from their homelands to live around the world, often blending with other peoples. Population matches may be divided between Global and Native to identify Diaspora affiliations as well as genetic links to indigenous peoples. For instance, African-Americans may match African Diaspora populations such as African-Americans from various U.S. States, Afro-Brazilians and related peoples. However, their Native Population Match results can also indicate roots in indigenous African, European or American Indian populations.

According to example embodiments, methods may include a Native Population Match to determine an individual's most likely genetic match with a subset of Global populations identified as Native. The term "Native Populations" as used herein is intended to encompass those that have experienced minimal admixture for example, within the past 500 years or so. The amount of admixture and/or the number of years over which such admixture has occurred may vary. But the idea is that a match may be performed specifically directed toward populations that have experienced significantly less admixture in recent years than other populations. Minimal admixture may be for example, 20% or less, 10% or less, or 5% or less over the last 100, 200, 300, 400, 500 or more years. These methods are intended to try to exclude e.g., variations in world population data caused by significant admixture of populations in recent years in certain populations, for example in the U.S. or Canada having a high degree of admixture. By way of non-limiting example, Native populations may include Native Amazonians, Scottish, Egyptians or Japanese. As with Global Population Match results, the most likely genetic matches in a Native Population Match may then be presented with by their match likelihood index (MLI) scores. For instance, a Native Population Match with Macedonia having an MLI score of 45.2 indicates that the individual's genetic ancestry is 45.2 times as likely in Macedonia as in the generic population (e.g., the world). Such information regarding native populations to which the individual most likely matches, whether expressed by MLI score or other measure of likelihood, may then be presented for example, to the individual, by use of a map or otherwise as discussed throughout this application.

According to example embodiments, methods may include a World Region match to determine an individual's most likely genetic match with World Regions. World Regions may be major biogeographic clusters or subdivisions of human genetic diversity or may be determined using medians or means of multiple member populations, rather than a "cluster representative." World Region match results may indicate an individual's most likely continent(s) of origin, and can indicate whether an individual is of mixed or relatively unmixed continental ancestry. As with other types of match results, the most likely genetic matches in a World Region match may then be presented with a match likelihood index (MLI) score. Such information regarding native populations to which the individual most likely matches, whether expressed by MLI score or other measure of likelihood, may then be presented for example, to the individual, by use of a map or otherwise as discussed throughout this application.

According to example embodiments, the present methods may provide a likelihood of an autosomal (e.g., STR or SNP) DNA profile of an individual in several World Regions. World Regions may be compared to individual populations to assist in determining an individual's most likely region of ancestry. The map depicted at FIG. 1 illustrates approximate geographical boundaries of example World Regions in accordance with example embodiments. Even within the borders of regions, individuals can be found with genetic ties to neighboring and sometimes distant regions. As shown in FIG. 1, World Regions may include for example the following regions:

American Indian:
Arctic: Inuit (Eskimo) peoples of Alaska.
Athabaskan: Athabaskan speaking Dine peoples of Western North America.
Mexican: Native peoples of Mexico.
North Amerindian: Native peoples of the Great Plains region of North America.
Ojibwa Algonquian speaking Ojibwa of northeastern North America.
Salishan: Salish of the American Pacific Northwest.
Native Central and South American:
Amazonian: Peoples of the Amazon Basin
Andean: Peoples of the Andean Mountains of western South America, including the territories of the historical Inca Empire
Central American: Peoples of the Central American Isthmus and northern South America.
Mayan: The historically Mayan region of Mesoamerica.
Patagonian: The plains region of southern South America.
Mestizo ("mixed") (not shown). Native Americans who have blended with Europeans and (to a lesser degree) Africans in recent history. This blending is most typical of Latin American populations, but can also be found in English and French speaking regions of North America.
European and Near Eastern:
Aegean: The eastern Mediterranean and Anatolia region, including modern territories of Southern Italy and Sicily, Greece, and Turkey.
Arabian: The Arabian Peninsula
Eastern European: The Slavic speaking region of Eastern Europe.
Finno-Ugrian: The Uralic speaking region of Northeastern Europe.
Levantine: Populations along the coast of the eastern Mediterranean Sea.
Mediterranean: The Romance speaking region of Southern Europe.
Mesopotamian: The historical "Cradle of Western Civilization" including modern Iran, Iraq and nearby territories.
North African: Populations of the Atlas Mountains and Sahara Desert.
Northwest European: The Celtic and Germanic speaking region of Northwestern Europe.
Sub-Saharan African:
East African: The Great Lakes and Horn of Africa. This region is home to the source of the White Nile River and is united by the Swahili language.
Southern African: This southeastern region of Africa is home to Khoisan speakers as well as Bantu speaking cultures that have expanded from West Africa in ancient times.
West African: Coastal West Africa, the origin point for many African Diaspora communities now living around the world.
Central and South Asian
Altaian: Altaic-speaking peoples of Central Asia, including the homelands of the historically nomadic Turkic and Mongolic peoples who have invaded Europe, the Near East, India, China, and other neighboring lands.
Eastern India: The eastern Indian Subcontinent.
North India: Northern India, Pakistan and neighboring territories, including the homeland of the ancient Vedic civilization.
South India: The southern Indian Subcontinent, including the Dravidian speaking peoples of Tamil Nadu and many other cultures.
Pacific:
Australian: Aboriginal peoples of Australia and Papua New Guinea
Polynesian: Literally meaning "many islands," the Polynesian region includes related peoples living between Samoa and New Zealand in the west to Hawaii in the east.
East Asian Regions:
Japanese: The Japanese Archipelago.
Malay Archipelago: Island Southeast Asia.
North Chinese: This region includes the "cradle of Chinese civilization" along the Yellow River, and is home to not only northern Han Chinese, but also Koreans and Mongolic and Tungusic peoples.
South Chinese: Southern China, including southern Han Chinese as well as other ethnic groups.
Southeast Asian: Mainland Southeast Asia.
Tibetan: The region including the Himalayan Mountains and the Tibetan Plateau and extends to the western provinces of modern China.

Rather than relying on presumed racial or ethnic divisions, the inventors have defined World Regions by objective mathematical criteria. In particular, World Regions have been identified by the present inventors using statistical analysis of a global DNA database of over 800 individual population samples around the world to identify groups of populations with shared genetic characteristics. These genetic groups may then be plotted on a map and named according to the geographical regions they occupy. It should be understood that as more data become available regarding population samples, and new population samples become available, World Regions may be updated and change. Such changes may include for example, changing of boundaries and/or names of regions within boundaries, or the addition or deletion of previously defined World Regions.

Each World Region represents a unique genetic family within the human species shaped by shared history and geography. Each region is characterized by a distinctive pattern of allele frequencies across the genetic loci studied. Although all humans are connected by ancient common origins, each of these genetic families shares a unique relationship due to more intense and persistent contacts within a geographical area. The present inventors have developed methods to distinguish these genetic families without relying on presumed racial or ethnic categories.

Figure 2:
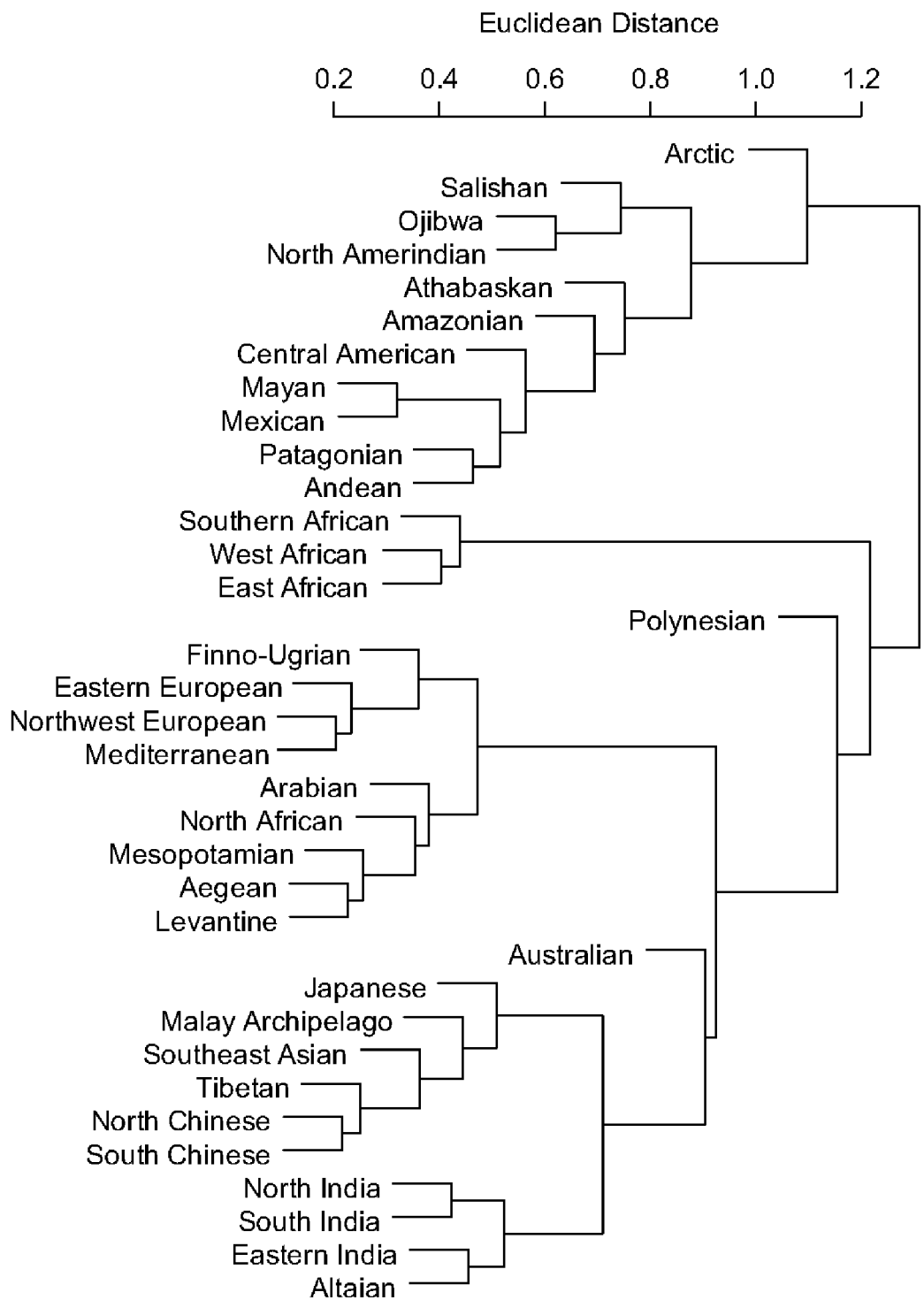
FIG. 2 is a diagram illustrating relationships between the illustrative World Regions of FIG. 1 using statistical analysis.

Hierarchical clustering may be performed on the World Region clusters with the distance metric as the sum of absolute differences. In the plots depicted at FIGS. 2 and 3, the distance between clusters is the average of the distances between the points in one cluster and the points in the other cluster. FIG. 2 depicts generally how example World Regions are related.

Figure 3:
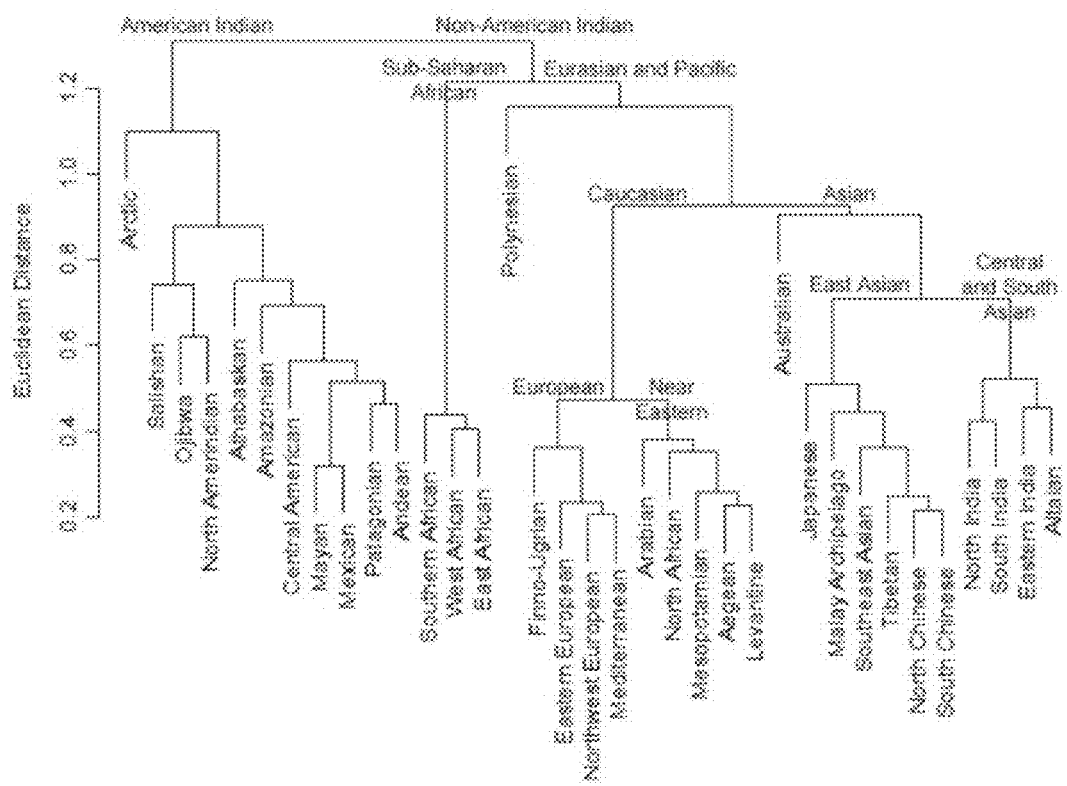
FIG. 3 is a diagram illustrating relationships between the illustrative World Regions of FIG. 1 using statistical analysis.

FIG. 3 illustrates the relationships between example World Regions identified by the inventors using statistical analysis. Closely related regions appear towards the bottom of the diagram. For instance, the Northwest European and Mediterranean regions are two of the most closely related of these regions. The deepest divisions appear at the top (root) of the tree. For instance, the Polynesian region is only distantly related to other World Regions and branches off alone towards the top of the tree diagram. Individual regions group together to form families and super-families of regions. Most of these larger groupings correspond to major continents. For instance, the East Asian regions (Japanese, Malay Archipelago, Southeast Asian, Tibetan, North Chinese, and South Chinese) form their own family. This East Asian family is part of a larger Asian super-family that also includes Central and South Asian (North India, South India, Eastern India, and Altaian) and Australian regions. Similarly, American Indian regions are part of their own super-family that is distinct from the Non-American Indian super-family that includes the other regions.

The relationships illustrated by FIG. 3 are the cumulative product of for example, (1) genetic contact within each region created by migrations, intermarriage, and gradual diffusion; and (2) relative isolation from other regions. Natural features that make these contacts easier or more difficult can determine regional relationships. Such natural features may include for example: waterways, mountain regions, fertile plains, and continental borders shape the pathways of human interactions that create both cultural areas and genetic regions. For instance, the historical difficulty of travel between Asia and North America corresponds to the great distance between the American Indian super-family and all other regions.

According to example embodiments, methods may include a Europa match to determine an individual's most likely genetic match with genetic sub-regions of Europe. As indicated above, the generic index population need not encompass the entire world. More detailed analyses may be performed using the methods described herein regarding populations within one or more continents or other subsets of the world. By way of non-limiting example, a more detailed analysis may be performed to determine genetic relationships in Europe using Europe as the generic index population, where the local populations are sub-regions of Europe. A comparison to genetic sub-regions of Europe may allow more specific identification of genetic relationships in Europe, including identification of local or private genetic characteristics not otherwise typical of major European World Regions.

As with World Regions, these Europa sub-regions are distinguished on an objective mathematical basis, and reflect long-term geographical and/or ethnic relationships within Europe. Some of these genetic territories correspond to modern political boundaries, but also reflect more ancient geographical relationships. For instance, the Greek genetic region includes not only modern Greece but also provinces of Southern Italy that were once part of Magna Grœcia (Greater Greece) in the classical world. Europa sub-regions may be biogeographic clusters or subdivisions of human genetic diversity or may be determined using medians or means of multiple member populations, rather than a "cluster representative."

As with other types of match results, the most likely genetic matches in a Europa match may then be presented with a match likelihood index (MLI) score. Such information regarding European sub-region populations to which the individual most likely matches, whether expressed by MLI score or other measure of likelihood, may then be presented for example, to the individual, by use of a map or otherwise as discussed throughout this application.

Figure 4:
FIG. 4 illustrates approximate geographical boundaries of illustrative European sub-regions according to example embodiments.

According to example embodiments, the present methods may provide a likelihood of an autosomal (e.g., STR or SNP) DNA profile of an individual in several European sub-regions. European sub-regions may be compared to individual populations to assist in determining an individual's most likely sub-region of ancestry within Europe. The map depicted at FIG. 4 illustrates approximate geographical boundaries of example European sub-regions in accordance with example embodiments. Even within the borders of regions, individuals can be found with genetic ties to neighboring and sometimes distant regions. As shown in FIG. 4, European sub-regions may include for example the following regions:

Spanish
Portuguese
Basque
Celtic
Norse
Germanic
Italian
Greek
Balkan
Ashkenazi
Polish
Finno-Ugrian
Russian Rather than relying on presumed racial or ethnic divisions, the inventors have defined European Sub-Regions by objective mathematical criteria. In particular, European sub-regions have been identified by the present inventors using statistical analysis of a global DNA database of numerous individual population samples in Europe to identify groups of populations with shared genetic characteristics. These genetic groups may then be plotted on a map and named according to the geographical regions they occupy. It should be understood that as more data become available regarding population samples, and new population samples become available, European sub-regions may be updated and change. Such changes may include for example, changing of boundaries and/or names of regions within boundaries, or the addition or deletion of previously defined European sub-regions.

Each European sub-region represents a unique genetic family within the human species shaped by shared history and geography. Each region is characterized by a distinctive pattern of allele frequencies across the genetic loci studied. Although all humans are connected by ancient common origins, each of these genetic families shares a unique relationship due to more intense and persistent contacts within a geographical area. The present inventors have developed methods to distinguish these genetic families without relying on presumed racial or ethnic categories.

Figure 5:
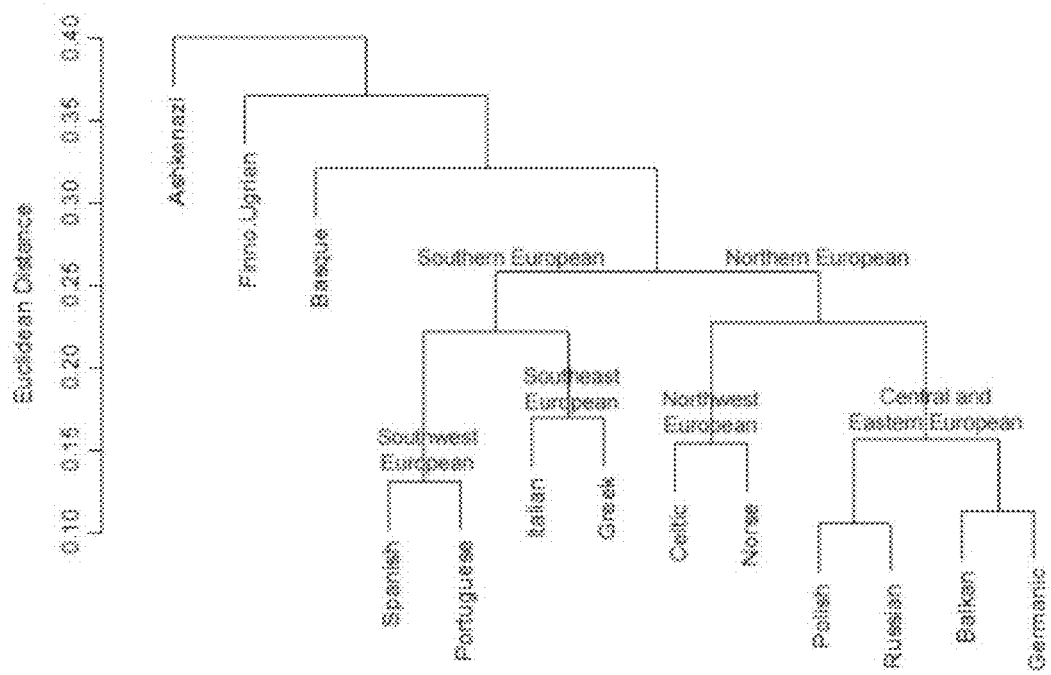
FIG. 5 is a diagram illustrating relationships between the illustrative European Sub-regions of FIG. 4 using statistical analysis.

Hierarchical clustering may be performed on European sub-region clusters with the distance metric as the sum of absolute differences. In the plot depicted at FIG. 5, the distance between clusters is the average of the distances between the points in one cluster and the points in the other cluster. FIG. 5 illustrates the relationships between European sub-regions identified by the present inventors. Closely related sub-regions appear towards the bottom of the diagram. For instance, the Polish and Russian regions are the two most closely related regions. The largest divisions appear at the top (root) of the tree. For instance, the Ashkenazi, Finno-Ugrian, and Basque sub-regions are only distantly related to other European sub-regions and branch off alone towards the top of the tree diagram. These unique genetic patterns found within these outlier sub-regions reflect relative isolation from other sub-regions due to cultural endogamy and/or geographical isolation.

In view of the above, example methods may include determining an individual's relative likelihood of a genetic match with one or more local European populations as compared to a generic index population, where the relative likelihood is determined by determining a genetic likelihood of the individual belonging to at least one local European population; determining a genetic likelihood of the individual belonging to a European generic index population; and comparing the likelihood of the individual belonging to the at least one local European population to the likelihood of the individual belonging to the European generic index population to determine the individual's relative likelihood of a genetic match with the one or more local European populations; wherein the local population is a European population and the European generic index population is an average or median of all European populations.

It should be understood that the Europa match is but one example of how the present methods may be used with respect to a generic index population that does not necessarily include the entire world, to provide more detailed information within a geographic region (such as a continent). It is contemplated that similar techniques may be applied to other continents or regions.

Further example methods may include implementing any of the present methods in an admixture analysis. A major flaw of present admixture testing is that it assumes a given individual is descended from presumed population references (usually representing standard racial categories). This creates errors when an individual is not, in fact, descended from these presumed sources of admixture. According to example embodiments, an individual's substantial match scores according to the present methods may be used to determine an admixture. For example, an individual's substantial match scores e.g., with World Regions, may be identified by a likelihood comparison. Then all World Regions for which the individual obtains a substantial likelihood score (e.g., greater than 1.0, or greater than the generic index) may be used as presumed sources of admixture in an admixture estimate. This eliminates the use of spurious admixture source populations not related to that individual. Thus, a World Region analysis can be used as one tier of a two-tiered admixture analysis.

Example embodiments are also directed to apparatuses that may include a server and software capable of performing methods herein. By way of non-limiting example, software may be capable of determining a first likelihood of an individual belonging to a local population by comparing genetic markers present in the individual to a frequency of such genetic markers occurring in the local population; and determining a second likelihood of the individual belonging to a generic index population by comparing the genetic markers present in the individual to a frequency of such genetic markers occurring in the generic index population. The software may be capable of comparing the first likelihood to the second likelihood. The software may be further be capable of determining a relative likelihood of the individual belonging to the local population as compared to the generic index population Alternatively, the software may be capable of calculating an individual's, a simulated individual's, and/or a group of actual individual members of a population's MLI scores. The software may also be capable of comparing such MLI scores. Example embodiments may include an apparatus comprising a server comprising software capable of determining an individual's relative likelihood of a genetic match with a local population as compared to a generic index population; determining one or more additional individual's relative likelihood of having a genetic match with the local population as compared to the generic index population; and comparing the individual's relative likelihood to the one or more additional individual's relative likelihood. The one ore more additional individuals may include simulated individuals or a group of actual individual members of a population. Determining at least one simulated individual's relative likelihood of having a genetic match with the local population as compared to the generic index population may include generating a distribution of likelihood scores for a population j using its observed allele frequencies.

Information regarding the frequency of genetic markers occurring in each population may be accessed by the server by various methods. The information may be stored in one or more databases that may be accessed separately, such as over the internet, or in a database coupled to the server (as in the systems described below).

Example embodiments also include systems that include a server coupled to a database. The database may include information regarding genetic markers occurring in at least one local population and/or in a generic index population. Information regarding genetic markers occurring in a generic index population might be a separate component of the database that also includes information regarding genetic markers occurring in at least one local population, or may be information derived from the information regarding the local population(s). As with other embodiments, in example embodiments, the server may include software capable of performing the methods herein, or a portion of such methods. For example, such software may be capable of determining a first likelihood of an individual belonging to a local population as compared to a generic index population by comparing genetic markers present in the individual to a frequency of such genetic markers occurring in the local population; and determining a second likelihood of the individual belonging to a generic index population by comparing the genetic markers present in the individual to a frequency of such genetic markers occurring in the generic index population. The software may be further capable of comparing the first likelihood to the second likelihood.

According to other embodiments, systems include a server coupled to a database where the server may include software capable of calculating an individual's and/or a simulated individual's (or group of actual individual's) MLI scores, and/or capable of comparing an individual's MLI score for a given population to MLI scores simulated for members of that population (or to MLI scores for a group of actual individuals of that population). In particular, embodiments may include a system that includes a server coupled to a database; wherein said database includes information regarding genetic markers occurring in at least one local population and information regarding genetic markers occurring in a generic index population; wherein the server comprises software capable of determining an individual's relative likelihood of a genetic match with a local population as compared to a generic index population; determining one or more additional (simulated or actual) individual's relative likelihood of having a genetic match with the local population as compared to the generic index population; and comparing the individual's relative likelihood to the one or more additional individual's relative likelihood.

Example embodiments are also generally directed to machine readable medium (such as a computer readable medium) that include code segments embodied on a medium that, when read by a machine, cause the machine to perform any of the present methods or portions thereof. Thus, example embodiments of a machine readable medium may include executable instructions to cause a device to perform one or more of the present methods or portions thereof.

Example embodiments also include computer-readable program products that include computer-readable medium and a program for performing one or more of the present methods or portions thereof.

A medium (such as a machine-readable medium or computer-readable medium) may include any medium capable of storing data that can be accessed by sensing device such as a computer or other machine. A machine-readable medium includes servers, networks or other medium that may be used for example in transferring code or programs from computer to computer or over the internet, as well as physical machine-readable medium that may be used for example, in storing and/or transferring code or programs. Physical machine-readable medium includes for example, disks (e.g., magnetic or optical), cards, tapes, drums, punched cards, barcodes, and magnetic ink characters and other physical medium that may be used for example in storing and/or transferring code or programs.

Example embodiments are also directed to kits that include at least one device for determining genetic markers of an individual and a machine readable medium that includes a medium and a program. The program may be for example, capable of determining a relative likelihood of an individual belonging to a local population as compared to a generic index population.

Example kits may be capable of calculating an individual's and/or a simulated individual's MLI scores (or MLI scores for a group of individuals of that population), and/or capable of comparing an individual's MLI score for a given population to MLI scores simulated for members of that population (or MLI scores for a group of individuals of that population). Kits provided herein may include at least one device for determining genetic markers of an individual; and a machine readable medium comprising a medium and a program capable of determining an individual's relative likelihood of a genetic match with a local population as compared to a generic index population; determining one or more additional individual's relative likelihood of having a genetic match with the local population as compared to the generic index population; and comparing the individual's relative likelihood to the one or more additional individual's relative likelihood.

Example devices for determining genetic markers of an individual may include at for example, a sample collector (such as a swab capable of collecting DNA). Other example devices may include a device capable of reading DNA from a sample collector, such as a device into which a swab may be inserted.

The following examples illustrate non-limiting embodiments. The examples set forth herein are meant to be illustrative and should not in any way serve to limit the scope of the claims. As would be apparent to skilled artisans, various changes and modifications are possible and are contemplated and may be made by persons skilled in the art.

Example 1

In this example, observed allele frequency data was used to simulate 2000 individual genetic profiles for studied world populations. Each simulated profile was processed using the present methods, and in particular using an algorithm, which measured the simulated individual's occurrence frequency in each of the World Regions. The strongest regional match was then identified for each simulated individual. These primary matches were then tallied for all simulated profiles to produce regional affiliation proportions.

The individual populations include a spectrum of regional affinities. This study (the results of which are depicted in FIGS. 6-9) illustrates the composition of individual ethnic and national populations. FIG. 6 illustrates American Indian populations. FIG. 7 illustrates European and Near Eastern populations. FIG. 8 illustrates Sub-Saharan African and Central and South Asian populations. FIG. 9 East Asian and Pacific populations.

As indicated above, as more data is incorporated and a statistical analysis is refined, a map of example World Regions may be clarified and refined. However, a number of basic points have become apparent as a result of inter alia, this study. First, American Indians, traditionally considered a homogeneous group or perhaps a minor offshoot of the Asian "Mongolian race," are instead a diverse family of autonomous World Regions. The genetic Gap between American Indian and all non-American Indian populations (geographically corresponding to the Bering Sea) represents the most significant division in world populations.

Second, intermediate regions within Eurasia are not equivalent to hypothetical admixtures between far Western Europeans and far Eastern Asians. Analysis of non-coding regions indicates Anatolians, Mongolians, North Indians and others possess unique genetic characteristics not explained by a simple racial admixture model.

Third, South Asia is the home of at least several unique World Regions not consistent with a simple model of East-West contact. Each of the North India, South India, and Eastern India regions is characterized by distinct allele frequencies, suggesting each of these places has become a unique genetic homeland rather than only a recipient of migrations.

Additionally, the Australian and Polynesian peoples are genetic outliers within the broader family or Eurasian regions, with no close relatives outside of their territorial homelands.

Mongolians proper are affiliated with an Altaian world region that bears only a distant relation to East Asians.

The cultural term "Hispanic" as used in the United States describes genetically disparate populations descended from American Indian, European and African ancestors, most of which share substantial affiliation with a Mestizo world region.

Further, many diaspora ethnic groups retain traces of their origins as well as their current homes. For instance, Polish Tatars are descended from Central Asians and retain Mongolian genetic affiliations as well as affiliations with European populations.

Example 2

In this example, observed allele frequency data was used to simulate 2000 individual genetic profiles for studied Europa sub-regions. Each simulated profile was processed using the present methods, and in particular using an algorithm, which measured the simulated individual's occurrence frequency in each European sub-region. The strongest regional match was then identified for each simulated individual. These primary matches were then tallied for all simulated profiles to produce regional affiliation proportions.

Individuals within each Europa sub-region obtain a spectrum of regional genetic affinities. Because of close genetic relationships within Europe, individuals in a sub-region can inherit genetic material that is most common in other sub-regions. Individuals from sub-regions with a history of ethnic endogamy or geographic isolation (such as the Ashkenazi, Basque, or Celtic sub-regions) exhibit higher frequencies of primarily in-group genetic affiliation. Individuals from centrally located sub-regions, such as the Balkan or Germanic regions, exhibit more variety in genetic affiliations and lower frequencies of primarily in-group genetic affiliation.

Figure 10:
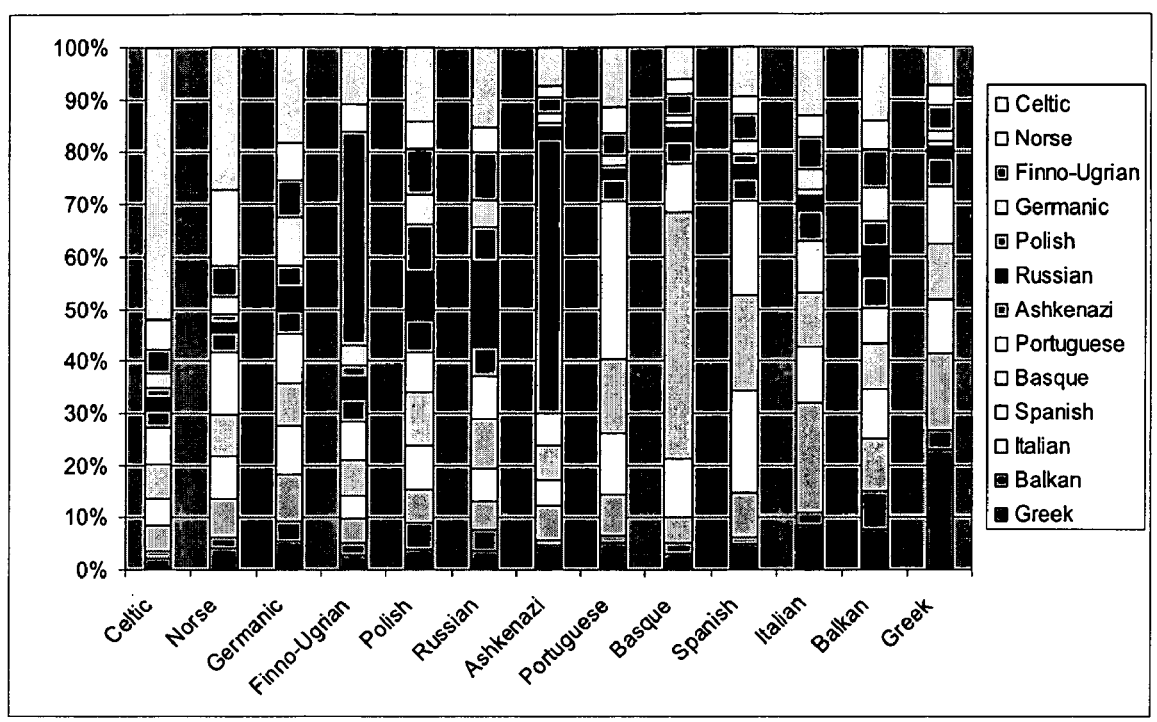
FIG. 10 is an illustration of the range of individual affiliations observed within each Europa genetic sub-region as determined by example methods.

This study (the results of which are depicted in FIG. 10) illustrates the range of individual affiliations observed within each Europa genetic sub-region.

Example 3

Individuals within each population exhibit a characteristic range of World Region (and Europa sub-region) scores. In this example, characteristic ranges were determined for three major U.S. Ethnic Groups. The tables depicted in FIGS. 11-14 list scores by percentile for Caucasians, African-Americans and Hispanics living in the United States. FIG. 11 depicts characteristic World Region scores of Caucasians (U.S.A.), FIG. 12 depicts characteristic Europa Sub-Region scores of Caucasians (U.S.A.), FIG. 13 depicts characteristic World Region scores of African Americans (U.S.A.), and FIG. 14 depicts characteristic World Region scores of Hispanics (U.S.A.). These percentiles provide the range of expected scores for individuals within each group.

As can be seen in FIG. 11, half of all U.S. Caucasians obtain a Northwest European score between 26.31 and 1,423.14, with a median of 182.19. Northwest European scores within this range could be considered ordinary for Caucasian individuals. Only five percent of Caucasians obtain a score either below 1.90 or above 25,825.32. These could be considered very low and very high scores within this ethnic group, respectively.

As can be seen in FIG. 12, half of all U.S. Caucasians obtain a Norse score between 25.02 and 1,350.58, with a median of 192.90. Norse scores within this range could be considered ordinary for Caucasian individuals. Only five percent of Caucasians obtain a score either below 1.79 or above 22,996.43. These could be considered very low and very high scores within this ethnic group, respectively.

As can be seen in FIG. 13, half of all African-Americans obtain a West African score between 1,150.84 and 2,792,606.95, with a median of 53,876.48. West African scores within this range could be considered ordinary for African-American individuals. Only five percent of African-Americans obtain a score either below 5.93 or above 1,621,469,999.23. These could be considered very low and very high scores within this ethnic group, respectively.

As can be seen in FIG. 14, half of all U.S. Hispanics obtain a Mestizo score between 8.47 and 199.42, with a median of 2,623.65. Mestizo scores within this range could be considered ordinary for U.S. Hispanic individuals. Only five percent of U.S. Hispanics obtain a score either below 0.87 or above 2,623.65. These could be considered very low and very high scores within this ethnic group, respectively.

Example 4

In this example, a Global Population database is used containing N (in this case 280) populations, each including a varying number of individuals. Population data is extracted from studies published in academic journals, including sources such as forensic science journals, and assembled with standard spreadsheet software. For each population j, the frequency p of individuals having a certain allele value at 13 STR loci was recorded. FIG. 15 shows an example distribution of frequencies for a subset of a Global Population database at the allele D8S1179. As mentioned above, as new population samples become available, World Regions may be updated and changed. This example was conducted using previous population data and World Regions previously described in parent U.S. patent application Ser. No. 11/621,646.

World Regions are identified as follows: a standard K-means clustering algorithm was used to separate all the populations in the Global Population database into k=4 distinct clusters (groups). These clusters correspond to major continental regions (European, Sub-Saharan African, East and South Asian, and American Indians). For each group k, a single population with the smallest Euclidian distance measure to the cluster's centers may be selected as representative of the group. Each of these four representative populations may be used as a reference point for the entire cluster, to which individuals are compared to estimate their continental ancestry for the World Region Match portion of analysis, as described below.

According to this example, genetic information is collected from an individual as follows: an autosomal STR profile is obtained for an individual, by collecting DNA from the individual using a standard cheek swab and his/her allele values at 13 autosomal STR loci, including D8S1179, D21S11, D7S820, CSF1PO, D3S1358, THO1, D13S317, D16S539, VWA, TPOX, D18S51, D5S818, and FGA are sequenced. For each individual, there are a total of 26 values, as the individual receives a unique allele from each parent at each locus. A sample individual genetic profile is shown in FIG. 16. Depending on the method being implemented all or some of these markers may be implemented. For example, values from nine of these markers may be used to compute Native and Global population matches, while values from all thirteen markers may be used to compute high resolution World Region matches.

Next, a GeoGenetic match for an individual may be produced by executing the following algorithm:
Step 1: For each population j, the frequencies matching the individual's allele value at each locus w, w=1 . . . 26 (where 26 is 2N and N is the number of autosomal loci), are extracted from the database. Then, the joint probability Pj of an individual matching jth population is computed by multiplying the extracted proportions, as follows:

$$P_j = \prod_{w=1}^{2N} p_{w|j}$$

wherein $p_{w|j}$ is a frequency of the individual's allele value at each locus w in population j, w=1 ... 2N, where N is the number of genetic loci for which data are collected from the individual.

Step 2: To account for sample size variation among populations, 95% confidence intervals (CI) for the joint probability that an individual belongs to a population j are obtained using the delta method. Then, the lower bound of this CI (denoted by tilde) is taken as a joint matching probability instead, as follows:

$$\tilde{P}_j = \exp\left\{\log P_j - Z_C \sqrt{\frac{1}{n_j} \sum_{w=1}^{2N} \frac{1 - p_{w|j}}{p_{w|j}}}\right\}$$

wherein $n_j$ is the number of individuals in population j for which genetic data were collected, and $Z_C$ is a z-score corresponding to the C confidence level.

Step 3: To make the interpretation of the lower bound of the 95% CI for all j meaningful, a synthetic Generic Human Index (GHI or GI) population is produced. This is done by averaging the frequencies for each specific allele for all populations and assuming that the sample size for GI population is the average of all population sample sizes, as follows:

$$P_{GI} = \prod_{w=1}^{2N} p_{w|GI}$$

where $p_{w|GI}$ is a frequency of matching the individual's allele value at each locus w, w=1 ... 2N, and N is the number of genetic loci for which data is collected from the individual. The lower bound of the 95% CI for the joint probability that an individual belongs to the GI population is calculated as follows:

$$\tilde{P}_{GI} = \exp\left\{\log P_{GI} - Z_C \sqrt{\frac{1}{n_{GI}} \sum_{w=1}^{2N} \frac{1 - p_{w|GI}}{p_{w|GI}}}\right\}$$

where $n_{GI}$ may be determined by the following formula:

$$n_{GI} = \frac{1}{K} \sum_{j=1}^{K} n_j$$

where K is a number of local populations used to calculate the generic index population, and $n_j$ is a number of individuals comprising local population j.

Step 4: A Match Likelihood Index (MLI or LR) is then produced for each population j by the following formula:

$$LR = \tilde{P}_j / \tilde{P}_{GI},$$

wherein $\tilde{P}_j$ is a joint probability of an individual matching a local population j, adjusted for confidence; and $\tilde{P}_{GI}$ is a joint probability of an individual matching a global index population GI, adjusted for confidence.

Step 5: The MLIs (or LRs) may then be ranked, with the populations having the highest scores considered the best matches for the individuals.

FIG. 17 presents an example of partial matching results for a Basque individual. The numbers to the left of each population are allele values and the numbers to the right of each allele value is its frequency in that particular population sample. The results in FIG. 17 are the ten most likely matching populations, in order with the most likely matching population at the top.

This matching procedure may be repeated multiple times using multiple groups of reference populations. By way of example, a Global Population Match, Native Population Match and/or World Region Match may be performed. For Global Population Match, the individual profile is matched to all populations in the Global Population Database. For Native Population Match, the individual profile is matched to a subset of populations designated as Native (that is, the ones that have experienced minimal post-Colonial admixture in the last 500 years). For World Region Match, the individual profile is matched to four populations identified as representatives of continental clusters.

Figure 18:
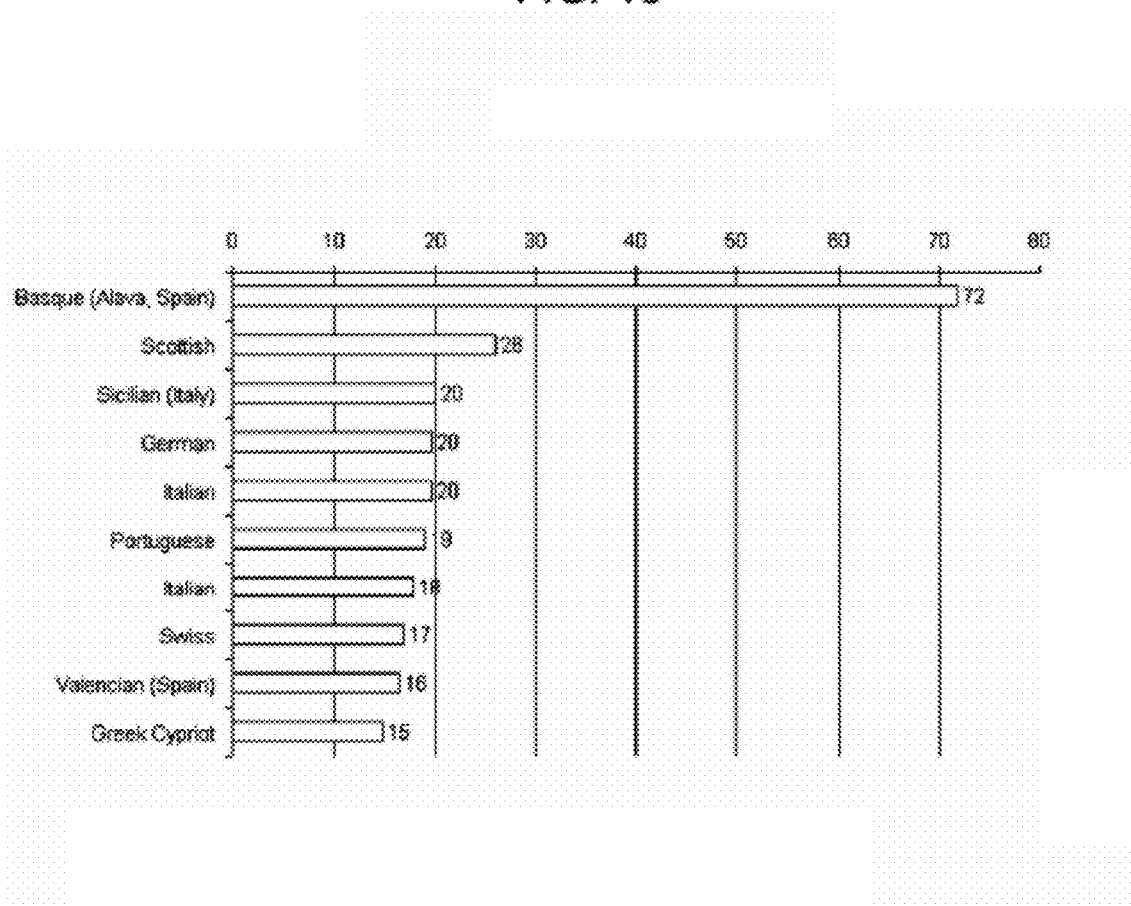
FIGS. 18 and 19 illustrate Native Population Match results for the individual of FIG. 17 according to example embodiments, where
Figure 19:
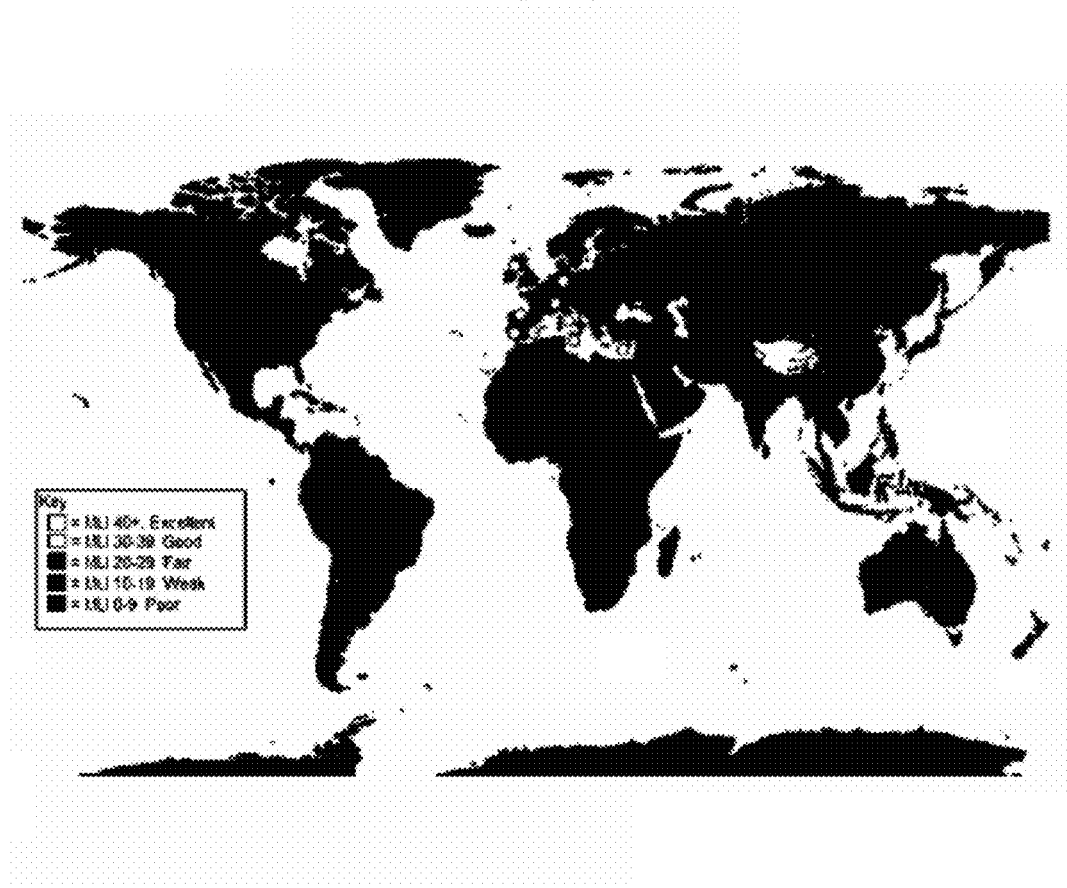
Figure 20:
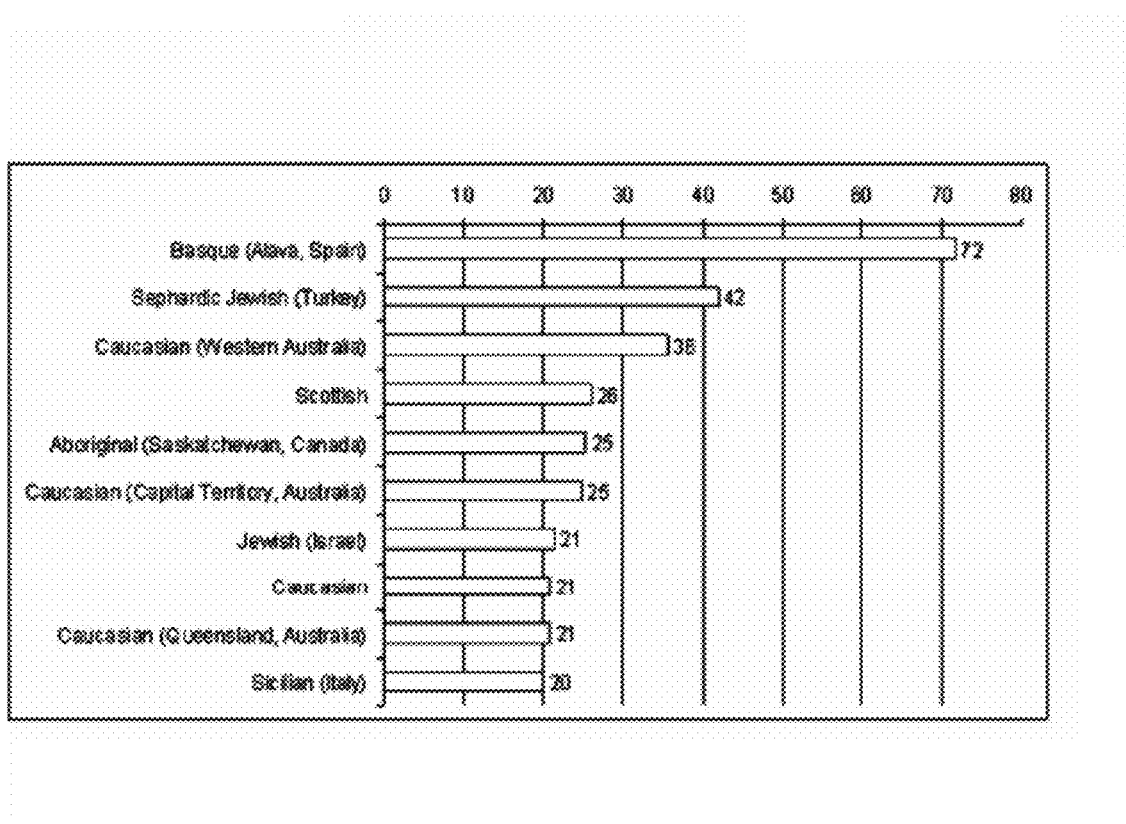
FIGS. 20 and 21 illustrate Global Population Match results for the individual of FIGS. 17-19 according to example embodiments, where
Figure 21:
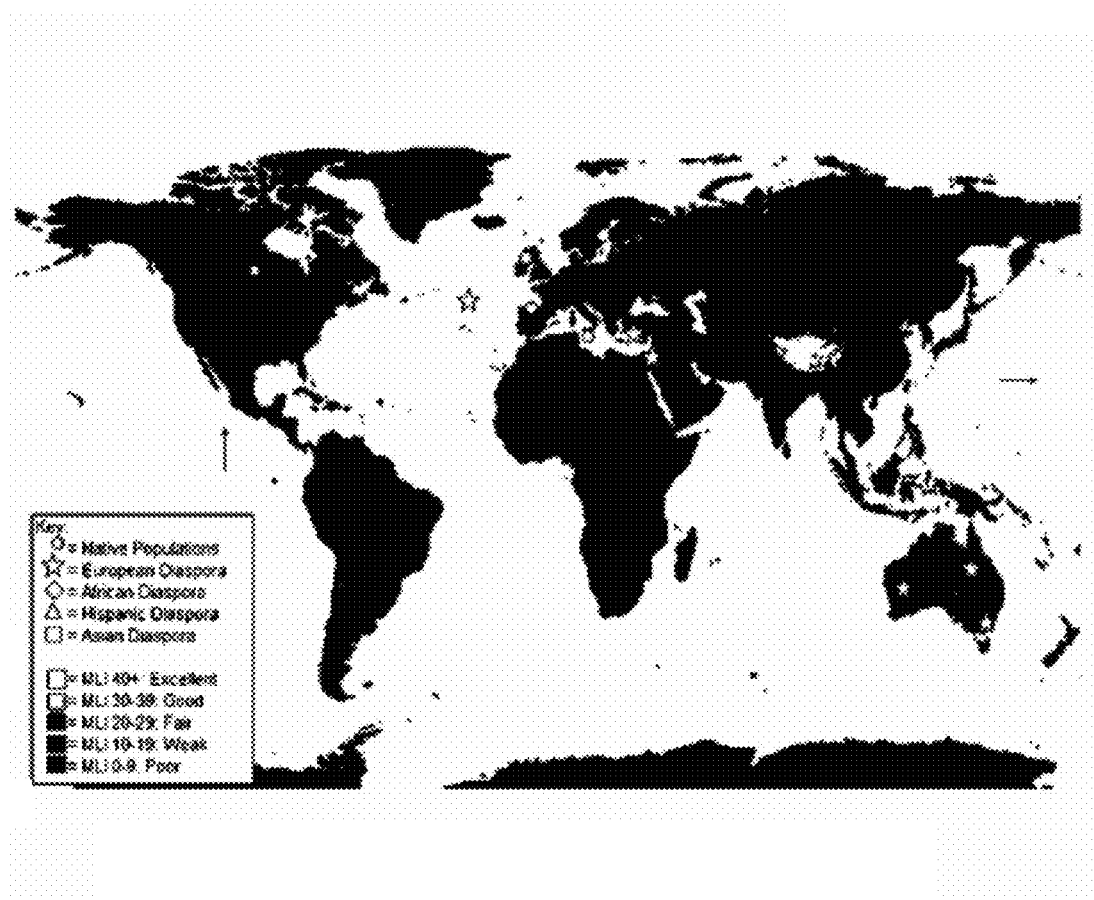
Figure 22:
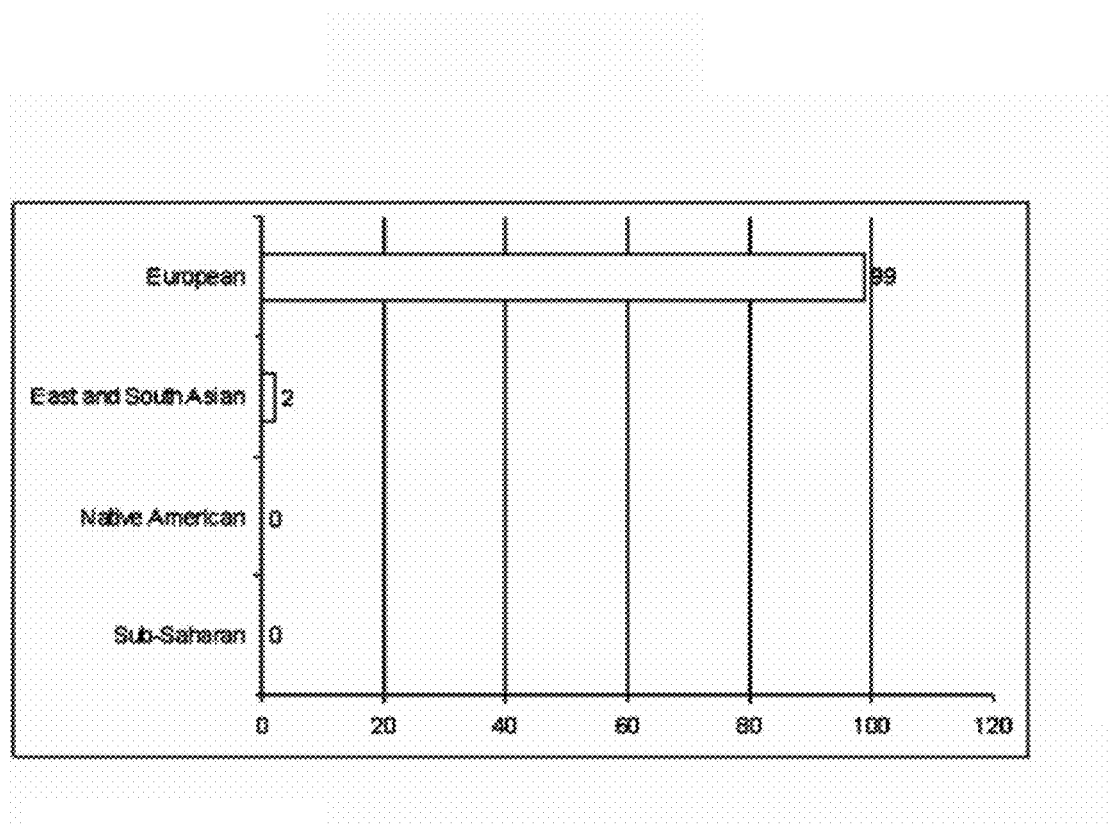
FIG. 22 illustrates numerical World Region Match results for the individual of FIGS. 17-21 according to example embodiments.

The final output of this analysis for an individual is displayed in FIGS. 18-22. FIGS. 18 and 19 illustrate Native Population Match results. FIGS. 20 and 21 illustrate Global Population Match results. FIG. 22 illustrates World Region Match results.

By using matches presented in multiple formats such as the Global Population Match, Native Population Match, and World Region Match of this example, this technique more accurately identifies the populations where an individual profile is most likely to occur, and estimates an individual's ethnic origin with a high degree of geographical precision. The use of confidence intervals and comparison of each match to a Generic Human Index population allows match results to be measured in terms of likelihood and specificity.

Example 5

In this example, the DNA of an African individual was used in the present methods. First genetic markers in the individual were determined by sequencing the individual's allele values from a sample of the individual's DNA at 13 autosomal STR loci. Values from nine of these markers were used to compute Native and Global population matches, while values from all thirteen markers were used to compute high resolution World Region matches. This example was also conducted using previous population data and World Regions previously described in parent U.S. patent application Ser. No. 11/621, 646. The allele values at each locus for the individual are set forth in FIG. 23.

Figure 24:
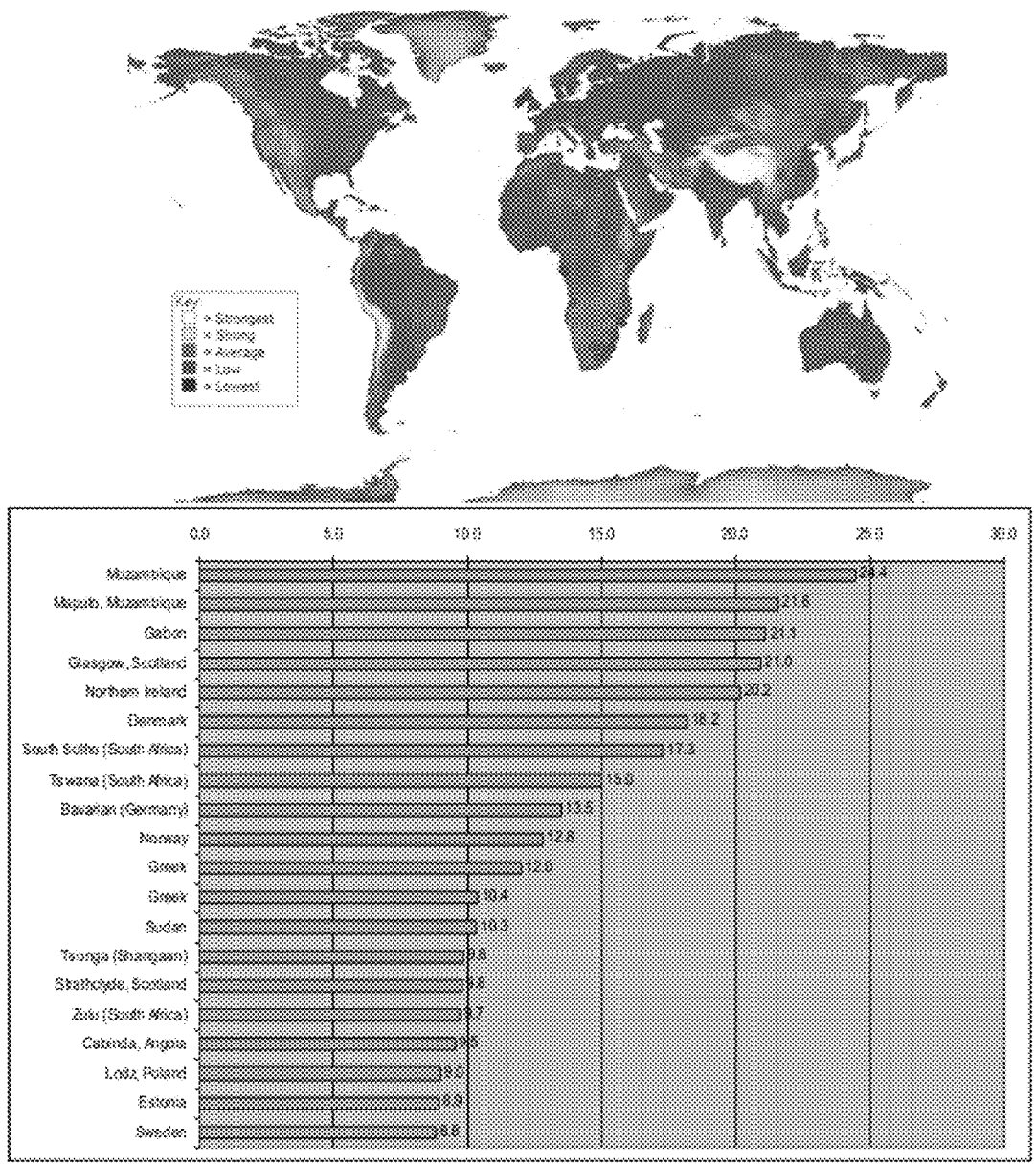
FIG. 24 is an illustration (both numerically and on a world map) of the top twenty Native population matches for the individual of FIG. 23 after performing a Native Population Match in accordance with example methods.

Referring to FIG. 24, the top twenty Native population matches for this individual include both European and African populations. Individual scores do not indicate a person's percentage of individual ethnic groups. Instead, they indicate where a DNA profile is most frequent. As shown in FIG. 24, the strongest match for this individual using population data available at the time of the calculations, is with a Mozambique sample, where this individual's DNA profile is 24.4 times as likely as in the world as a whole. However, this DNA profile can be found in other nearby African populations at similar frequencies. For instance, the score for Gabon is 21.1, indicating this DNA profile is 24.4/21.1=1.2 times as likely in Mozambique as in Gabon.

Some nations appear multiple times within these listings. For instance, samples from Mozambique and Maputo, Mozambique appear at similar frequencies. These represent independent population samples. When two samples from the same nation obtain similar scores, this is more evidence of genetic connections to this nation or ethnic group.

For this individual, Mozambique would be the most likely African place of origin, but other ethnic origins such as Gabon, South Sotho, or Sudan cannot be excluded. Because no population is completely isolated from its neighbors, individual DNA profiles often overlap with a number of populations at similar frequencies. These genetic matches provide strong clues as to where this person's ancestors left the strongest genetic traces and where their genetic relatives in Africa live today.

FIG. 24 also shows that this individual's top matches also include European populations, indicating an element of European ancestry. Within Europe, this person's DNA profile is most frequent within Glasgow, Scotland, suggesting Scottish ancestors or ancestors from the British Isles.

A Global Population Match may then be performed which may provide for example, the individual's top twenty matches in a database of all global populations, including native peoples as well as Diaspora groups that expanded from their homelands and sometimes admixed with other populations in recent history. Results of this individual's Global Population Match are depicted in FIG. 25.

For the individual tested, the Global results include not just native African populations but also the African Diaspora. For instance, this individual's DNA profile can be found at high frequencies in African-Americans living in many places, from the Bahamas to Connecticut. Global Population Matches do not mean this individual's ancestors came from the Bahamas or Connecticut, but indicate places where African-Americans of a similar genetic background live today.

A High Resolution World Region Match was then performed, which measures an individual's genetic connections to World Regions. World Regions according to Examples 5 and 6 were defined and determined somewhat differently than in Example 4. In particular, Example 4 identifies World Region "cluster centers," that is, identifying a population sample that approximates an identified regional group. Examples 5 and 6 define World Regions using medians or means of multiple of member populations rather than a "cluster representative."

World Region results may provide the best general picture of a person's genetic connections to the world. They can often clarify individual Native and Global population match results when they are difficult to interpret. For instance, this individual's DNA profile (as shown in FIG. 26) is most frequent in Sub-Saharan Africa but can also be found (with scores>1.0) in other regions including Northwest Europe. This is consistent with the distribution of both Native and Global population matches, which are concentrated among populations of African descent but also include British Isles populations. To be more precise, this individual's DNA profile is most frequent in Sub-Saharan, where it is 163.4 times as likely as in the world. Substantial scores (>1.0) also include North Africa, Arabia, Asia Minor, Northwest Europe, the Mediterranean, Eastern Europe and North India. These secondary affiliations indicate this DNA profile can also be found at lower frequencies in other World Regions.

Scores can be compared to each other to give relative frequencies. For instance, this DNA profile is 163.4/19.6=8.3 times as frequent in Sub-Saharan Africa as in North Africa. All scores were measured against the Generic Human Index (GHI or GI) of 1.0. Scores above 1.0 are more frequent in that region than in the world, while scores below 1.0 are more frequent in the world than in that region. For instance, this individual's score for the Basque region is 0.1, indicating this DNA profile is 1.0/0.1=10 times as likely in the world as in the Basque region.

The results for this person provide a detailed and comprehensive picture of their African-American ancestry including their closest genetic relatives amongst ethnic groups in Africa, Europe and the African Diaspora as well as precise measurements of where their DNA profile can be found in the World Regions.

Example 6

In this example, the DNA of a European individual was used in the present methods. First genetic markers in this individual were determined by sequencing the individual's allele values from a sample of the individual's DNA at 13 autosomal STR loci. The allele values at each locus for the individual are set forth in FIG. 28. For instance, at locus TH01, this individual has inherited one allele of length 6 (6 repeats) and an allele of length 9.3 (9.3 repeats). Values from nine of these markers were used to compute Native and Global population matches, while values from all thirteen markers were used to compute high resolution World Region matches. Just as with the previous examples, this example was conducted using previous population data and World Regions.

Figure 28:
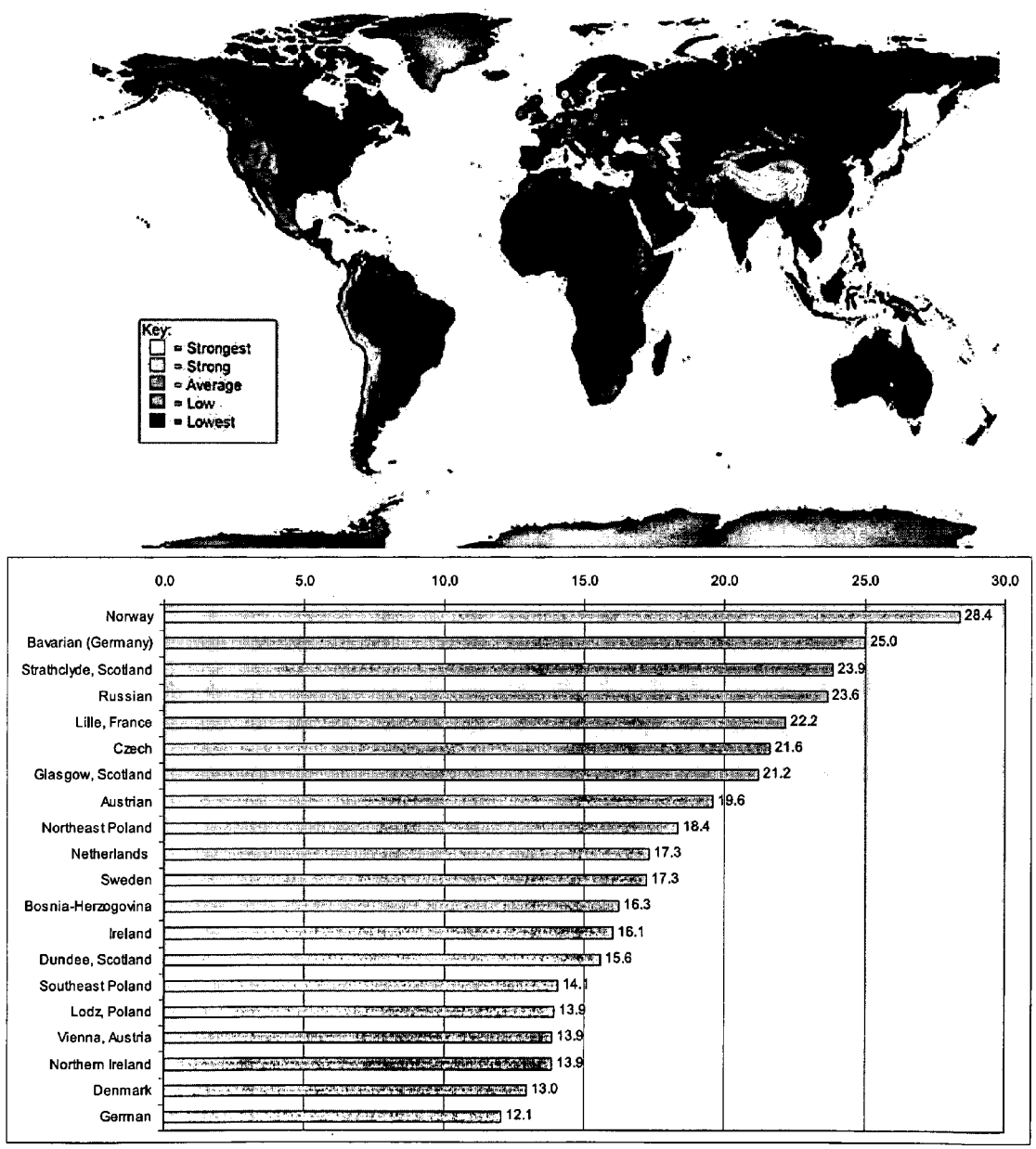
FIG. 28 is an illustration (both numerically and on a world map) of the top twenty Native population matches for the individual of FIG. 27 after performing a Native Population Match in accordance with example methods.

Referring to FIG. 28, this individual's top twenty matches in a database of all native populations that have experienced minimal movement and admixture in the last 500 years were determined by the present methods. Individual matches do not necessarily indicate recent social or cultural affiliation with a particular ethnicity. Rather, the geographical distribution of the individual's Native Population Match results indicates his most likely deep ancestral origins.

The top twenty Native population matches for this individual all fall within Europe. The strongest match is with a Norwegian sample, where this individual's DNA profile is 28.4 times as likely as in the world as a whole. However, this DNA profile can be found in other nearby European nations at similar frequencies. For instance, the score for Sweden is 17.3, indicating this DNA profile is 28.4/17.3=1.64 times as likely in Norway as in Sweden.

For this individual, Norway would be the most likely population of origin, but other ethnic origins such as Austrian, Irish or Dutch cannot be excluded. It is also possible this individual could be of Italian or French heritage but has inherited genetic markers that are more typical of more northerly parts of Europe.

Figure 29:
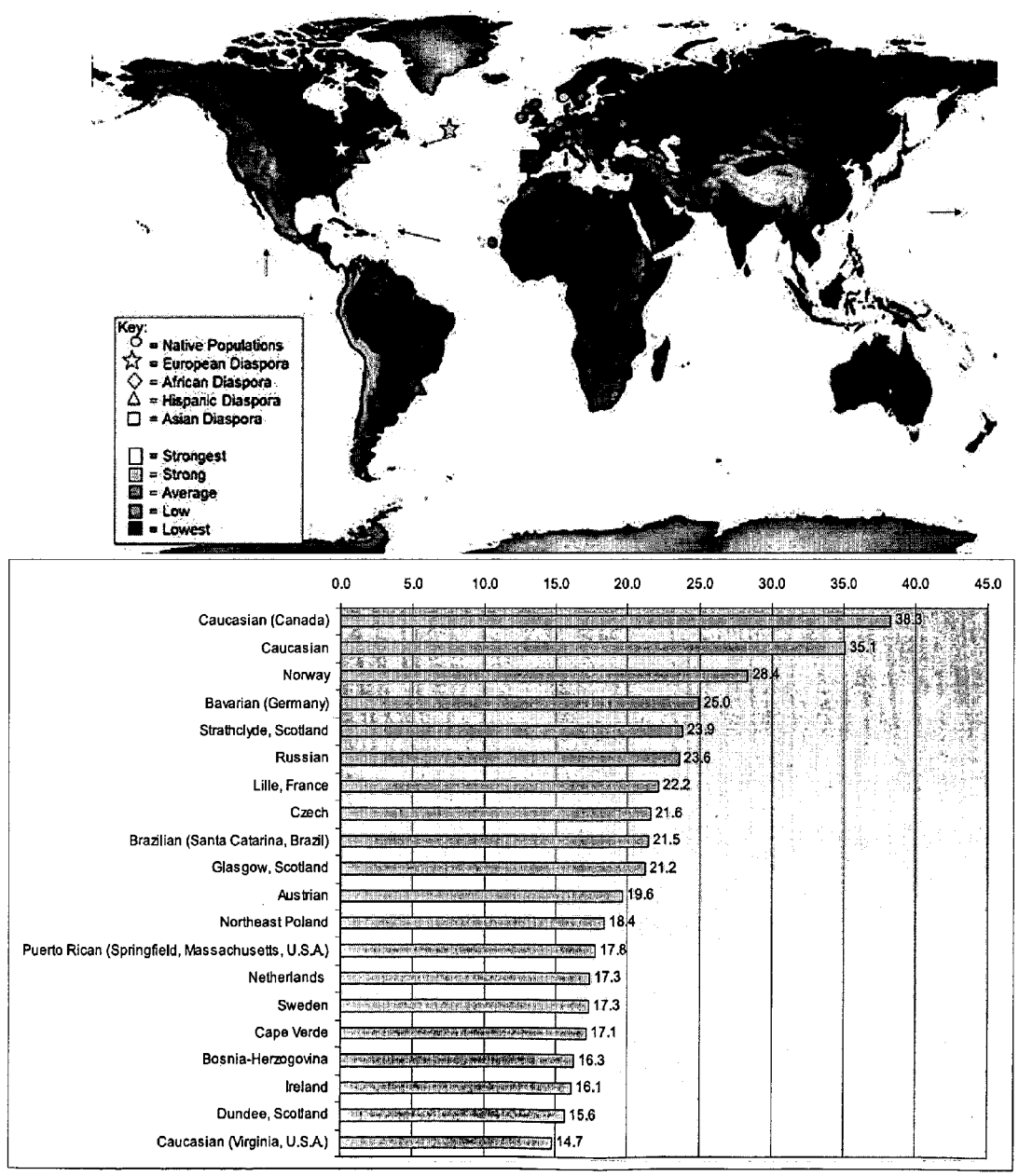
FIG. 29 is an illustration (both numerically and on a world map) of the top twenty Global Population matches for the individual of FIG. 27 after performing a Global Population Match in accordance with example methods.

Next, a Global Population Match was performed. The individual's top twenty matches in a database of all global populations, including native peoples as well as Diaspora groups that expanded from their homelands and sometimes admixed with other populations in recent history were provided. These Global results (as depicted in FIG. 29) include not just native European populations but also the European Diaspora. For instance, this individual's DNA profile can be found in Canadian Caucasians, Brazilians from Santa Catarina, Puerto Ricans and Virginia Caucasians at similar frequencies. Global Population Matches do not mean this individual's ancestors came from the Brazil or Virginia, but indicate places where Caucasians of a similar genetic background live today.

A High Resolution World Region Match was then performed, which measures an individual's genetic connections to World Regions. As depicted in FIG. 30, this individual's DNA profile is most frequent in Eastern Europe and Northwest Europe. This is consistent with the distribution of both Native and Global population matches, which are concentrated within these regions. To be more precise, this individual's DNA profile is most frequent in Eastern Europe, where it is 21.2 times as likely as in the world. Substantial scores (>1.0) also include Northern Europe, the Mediterranean, Asia Minor, Finno-Ugrian and Sub-Saharan African. These secondary affiliations indicate this DNA profile can also be found at lower frequencies in other World Regions.

Scores can be compared to each other to give relative frequency. For instance, the DNA profile for this individual is 21.2/15.4=1.37 times as frequent in Eastern Europe as in Northwestern Europe. This indicates that while this person's DNA is most common in Eastern Europe, it is nearly as common in Northwestern Europe. However, this DNA profile is 21.2/4.2=5.0 times as frequent in Eastern Europe as in the Finno-Ugrian region, indicating a stronger difference between these two regions.

All scores were measured against the Generic Human Index of 1.0. Scores above 1.0 are more frequent in that region than in the world, while scores below 1.0 are more frequent in the world than in that region. For instance, this individual's score for North India is 0.5, indicating this DNA profile is 1.0/0.5=2 times as likely in the world as in North India.

The results for this person provide a detailed and comprehensive picture of their European ancestry including their closest genetic relatives amongst ethnic groups in Europe and the European Diaspora as well as precise measurements of where their DNA profile can be found in the World Regions.

Example 7

The following is an example of a weak allele that according to certain embodiments would not be used in calculating matches. Let $p_j$ denote the proportion of individuals having specific allele value z in population j. The allele "z" is a "weak allele," and therefore will not be used in the calculations and methods herein, because it fails the following mathematical criteria:

a) $P_{max}/P_{95} < 3$, where $p_{max}$ is the maximum frequency observed in all populations at allele z of locus Z and $p_{95}$ is the 95% percentile value of the frequencies.

b) at least 90% of the top 20 populations with the highest $p_j$ values are in at most two World Regions.

In particular, the following allele value 13 of Gene D3S1358 is a "weak allele" because it fails both criteria as follows: as shown in Table 1, the ratio between the maximum frequency and the 95th percentile is 7.25, which is much larger than 3; as shown in Table 2, the top two World Regions represent only 65% (40% Indian and 25% Mediterranean) of the populations in the top twenty, that is, the twenty populations having the highest frequencies.

TABLE 1

| Locus |
| --- |
| D3S1358 |
| Allele Value |
| 13 |
| $p_{max}$ |
| 0.0366 |
| $p_{95}$ |
| 0.0051 |
| $p_{max}/p_{95}$ |
| 7.25 |

TABLE 2

| Population | Frequency | World Region | World Region | # in Top 20 | % of Top 20 |
| --- | --- | --- | --- | --- | --- |
| Katkari Tribal | 0.0366 | Indian | Indian | 8 | 40.00% |
| Uttar Pradesh Khatri | 0.0341 | Indian | Mediterranean | 5 | 25.00% |
| Khandait Orissa | 0.0284 | Indian | African | 3 | 15.00% |
| Oraon Chotanagpur Plateau | 0.0245 | Indian | Middle Eastern | 2 | 10.00% |
| Tutsi | 0.0169 | African | Mestizo | 1 | 5.00% |
| African Cape Town | 0.0143 | African | Southeast Asian | 1 | 5.00% |
| Qatar | 0.0114 | Middle Eastern | | | |
| Muslim Karnataka India | 0.0104 | Indian | | | |
| Maheli Tribal Bengal | 0.0103 | Indian | | | |
| Baniya Bihar | 0.0098 | Indian | | | |
| Kuvi Khond Tribal Orissa | 0.0096 | Indian | | | |
| Hutu | 0.0092 | African | | | |
| Thai | 0.0077 | Southeast Asian | | | |
| Mestizo Ecuador | 0.0071 | Mestizo | | | |
| Emilia Romagna Italy | 0.0071 | Mediterranean | | | |
| Calabria Italy | 0.0070 | Mediterranean | | | |
| Basque Alava | 0.0051 | Mediterranean | | | |
| Lazio Italy | 0.0051 | Mediterranean | | | |
| Iranian | 0.0050 | Middle Eastern | | | |
| Basque Guipuzcoa | 0.0049 | Mediterranean | | | |

Both criteria may vary. For example, as can be seen by this example, the second criterion is designed to ensure that an allele value is strongly associated with a small number of populations. Although the number of populations considered may be more or fewer than twenty, and the percentages required for the criteria to be met may vary, the goal is to make sure an allele value is strongly associated with only a small number of populations versus being spread all over the world. Just as with the immediately previous examples, this example was conducted using previous population data and World Regions.

Example 8

In this example, the DNA of a Korean individual was used in the present methods. First genetic markers in this individual were determined by sequencing the individual's allele values from a sample of the individual's DNA at 21 autosomal STR loci. The allele values at each locus for the individual are set forth in FIG. 31. For instance, at locus TH01, this individual has inherited one allele of length 7 (7 repeats) and an allele of length 9 (9 repeats). Values from all 21 markers were used to compute Native and Global population matches and high resolution World Region matches.

Referring to FIG. 25, this individual's top twenty matches in a database of 577 native populations that have experienced minimal movement and admixture in modern history (approximately, the last 500 years) were determined by the present methods. Individual matches do not necessarily indicate recent social or cultural affiliation with a particular ethnicity. Rather, the geographical distribution of the individual's Native Population Match results indicates his most likely deep ancestral origins.

As shown in FIG. 32, the strongest match for this individual is with a Korean sample, where this individual's DNA profile is 530.06 times as likely as in the world as a whole. For this individual, Korea would be the most likely population of origin, but other ethnic origins such as China and Japan cannot be excluded. FIG. 32 also shows in parentheses, a TribeScore for each of the top twenty matches. The TribeScore for the first Korean match is (0.94) indicating that the individual's MLI score is higher than 94% of scores from that particular Korean reference population.

Next, a Global Population Match was performed. The individual's top twenty matches in a database of 801 global populations, including native peoples as well as Diaspora groups that expanded from their homelands and sometimes admixed with other populations in recent history were provided. These Global results are depicted in FIG. 33 (which also shows the TribeScores for each region).

A High Resolution World Region Match was then performed, which measures an individual's genetic connections to World Regions. As depicted in FIG. 34, this individual's DNA profile is most frequent in North Chinese and Japanese regions. This is consistent with the distribution of both Native and Global population matches, which are concentrated within these regions. To be more precise, this individual's DNA profile is most frequent in North China, where it is 354.77 times as likely as in the world.

All scores were measured against the Generic Human Index of 1.0. Scores above 1.0 are more frequent in that region than in the world, while scores below 1.0 are more frequent in the world than in that region. For instance, this individual's score for Eastern Europe is 0.04, indicating this DNA profile is 1.0/0.04=25 times as likely in the world as in Eastern Europe.

FIG. 34 also shows in parentheses, a TribeScore for each of the top twenty matches. The TribeScore for the North Chinese region is (0.95) indicating that the individual's MLI score is higher than 95% of scores from the North Chinese World region. The World Region TribeScores not only indicate that the person is within the expected percentile range of (0.05) and above fore several regions, but also outside that expected range for other regions. This allows exclusion of origins from these other regions, which provides a second level of information to complement frequency-based MLI scores.

The results for this person provide a detailed and comprehensive picture of their Korean ancestry including their closest genetic relatives amongst ethnic groups in the North Chinese region.

Example 9

In this example, the DNA of a Malay (Singapore) individual was used in the present methods. First genetic markers in this individual were determined by sequencing the individual's allele values from a sample of the individual's DNA at 21 autosomal STR loci. The allele values at each locus for the individual are set forth in FIG. 35. For instance, at locus D19S433, this individual has inherited one allele of length 13 (13 repeats) and an allele of length 15.2 (15.2 repeats). Values from all 21 markers were used to compute Native and Global population matches and high resolution World Region matches.

Referring to FIG. 36, this individual's top twenty matches in a database of 577 native populations that have experienced minimal movement and admixture in modern history (approximately, the last 500 years) were determined by the present methods. Individual matches do not necessarily indicate recent social or cultural affiliation with a particular ethnicity. Rather, the geographical distribution of the individual's Native Population Match results indicates his most likely deep ancestral origins.

As shown in FIG. 36, the strongest match for this individual is with a Malay (Singapore) sample, where this individual's DNA profile is 663.32 times as likely as in the world as a whole. For this individual, Malay (Singapore) would be the most likely population of origin, but other ethnic origins such as Thailand, Javanese, and Indonesia cannot be excluded. FIG. 36 also shows in parentheses, a TribeScore for each of the top twenty matches. The TribeScore for the Malay (Singapore) match is (0.98) indicating that the individual's MLI score is higher than 98% of scores from that particular reference population.

Figure 37:
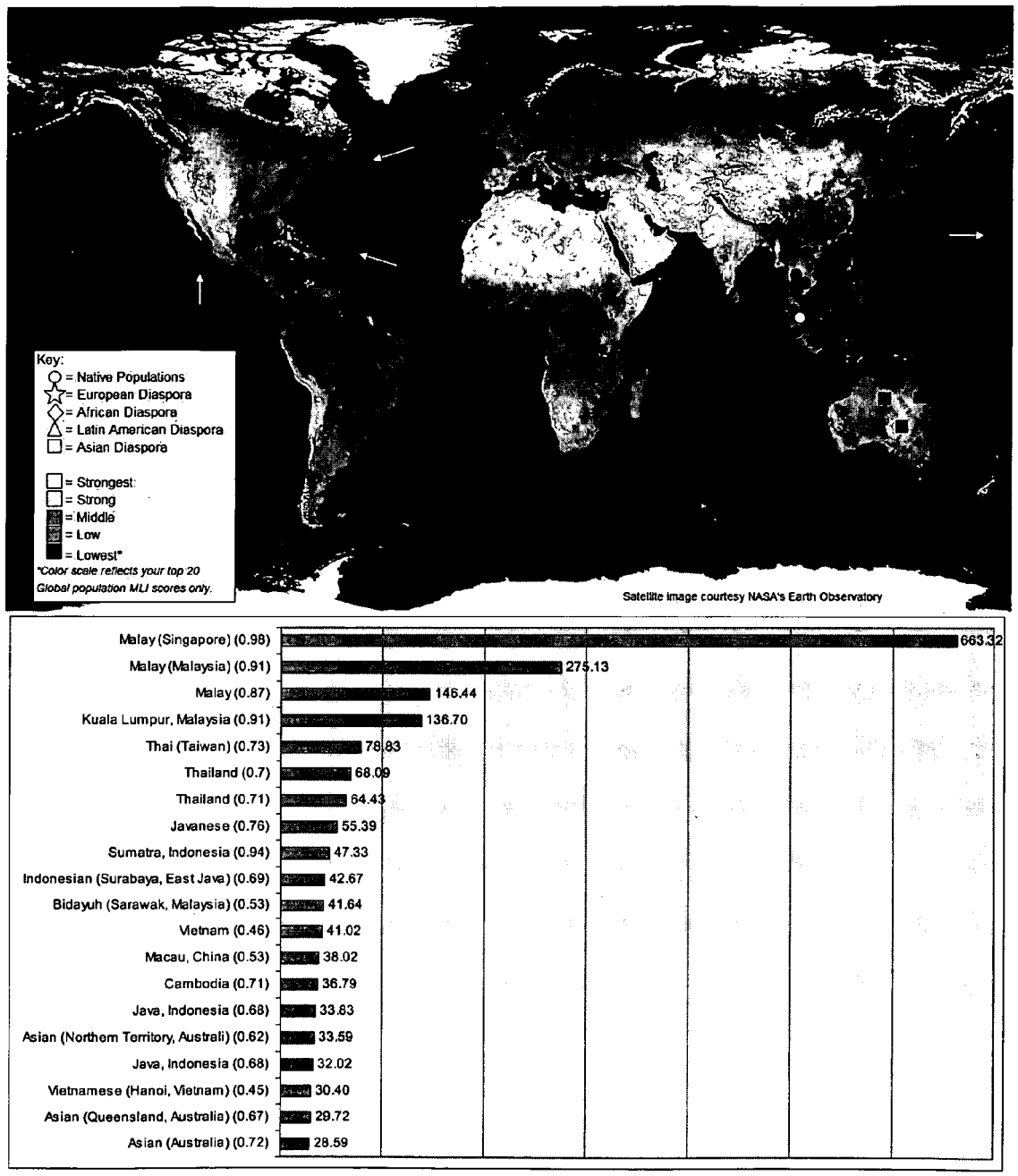
FIG. 37 is an illustration (both numerically and on a world map) of the top twenty Global Population matches for the individual of FIG. 35 after performing a Global Population Match in accordance with example methods.

Next, a Global Population Match was performed. The individual's top twenty matches in a database of 801 global populations, including native peoples as well as Diaspora groups that expanded from their homelands and sometimes admixed with other populations in recent history were provided. These Global results are depicted in FIG. 37 (which also shows the TribeScores for each region).

Figure 38:
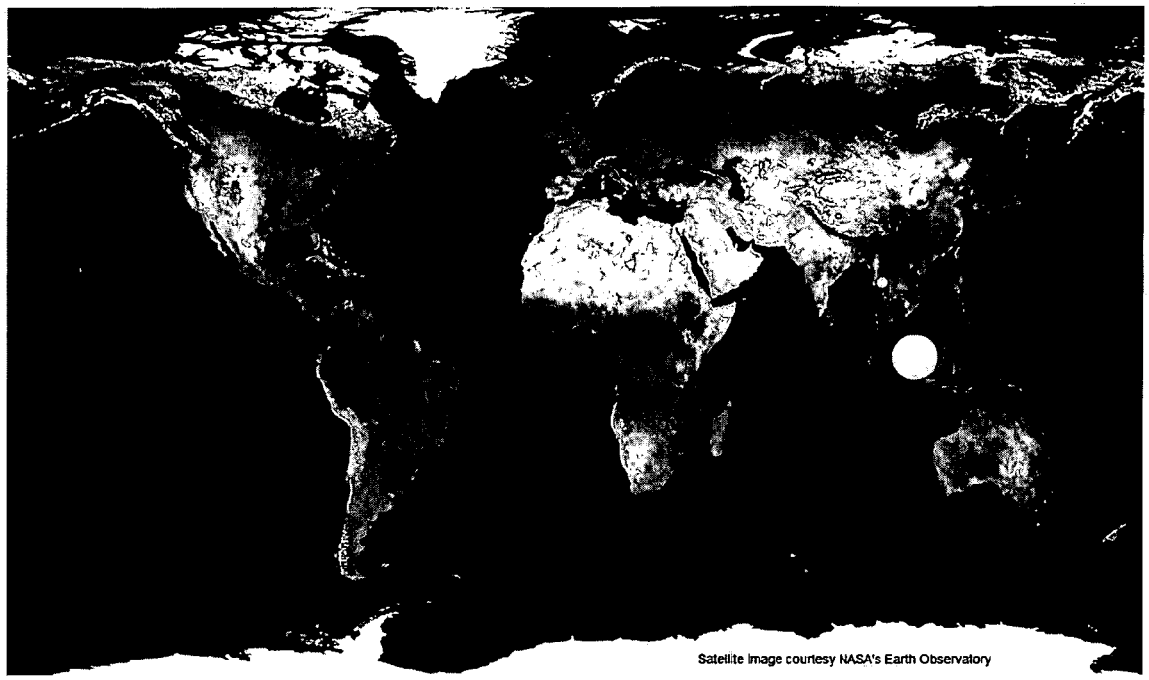
FIG. 38 is an illustration (both numerically and on a world map) of the top high resolution World Region matches for the individual of FIG. 35 after performing a World Region match in accordance with example methods.

A High Resolution World Region Match was then performed, which measures an individual's genetic connections to World Regions. As depicted in FIG. 38, this individual's DNA profile is most frequent the Malay Archipelago region. This is consistent with the distribution of both Native and Global population matches. This individual's DNA profile is most frequent in Malay Archipelago where it is 167.48 times as likely as in the world.

All scores were measured against the Generic Human Index of 1.0. Scores above 1.0 are more frequent in that region than in the world, while scores below 1.0 are more frequent in the world than in that region. For instance, this individual's score for Japanese is 0.06, indicating this DNA profile is 1.0/0.06=16.67 times as likely in the world as in Japan.

FIG. 38 also shows in parentheses, a TribeScore for each of the top twenty matches. The TribeScore for the Malay Archipelago region is (0.93) indicating that the individual's MLI score is higher than 93% of scores from the Malay Archipelago World region. The World Region TribeScores not only indicate that the person is within the expected percentile range of (0.05) and above fore several regions, but also outside that expected range for other regions. This allows exclusion of origins from these other regions, which provides a second level of information to complement frequency-based MLI scores.

The results for this person provide a detailed and comprehensive picture of their Malaysian ancestry including their closest genetic relatives amongst ethnic groups in the Malay Archipelago region.

Although the invention has been described in example embodiments, many additional modifications and variations would be apparent to those skilled in the art. For example, modifications may be made for example to the methods described herein including the addition of or changing the order of various steps. Modifications may be made to the example statistical analyses provided herein. Other examples of possible modifications may include modifications to the output that demonstrates calculated results, such as rankings, lists, maps, etc. It is therefore to be understood that this invention may be practiced other than as specifically described. Thus, the present embodiments should be considered in all respects as illustrative and not restrictive.

What is claimed is:

1. A computer-implemented method comprising
(a) determining, using a computer, an individual's relative likelihood of a genetic match with a local population selected from a group of reference local populations, as compared to a generic index population, said generic index population comprising the group of reference populations, wherein said individual's likelihood of belonging to a local population is determined from a product of the frequencies of occurrence in the local population of genetic markers present in the individual, and wherein said individual's likelihood of belonging to a generic index population is determined from a product of the frequencies of occurrence in the generic index population of genetic markers present in the individual;
(b) determining, using a computer, one or more additional individual's relative likelihood of having a genetic match with the local population as compared to the generic index population; wherein said additional individual's likelihood of belonging to a local population is determined from a product of the frequencies of occurrence in the local population of genetic markers present in the additional individual, and wherein said additional individual's likelihood of belonging to a generic index population is determined from a product of the frequencies of occurrence in the generic index population of genetic markers present in the additional individual; and
(c) comparing, using a computer, the individual's relative likelihood to the one or more additional individual's relative likelihood.

2. The computer-implemented method of claim 1, wherein determining an individual's relative likelihood of a genetic match with one or more local populations as compared to a generic index population comprises
determining, using a computer, a genetic likelihood of the individual belonging to at least one local population selected from a group of reference populations from a product of the frequencies of occurrence in the local population of genetic markers present in the individual;
determining, using a computer, a genetic likelihood of the individual belonging to a generic index population, said generic index population comprising the group of reference populations from a product of the frequencies of occurrence in the generic index population of genetic markers present in the individual; and
comparing, using a computer, the likelihood of the individual belonging to the at least one local population to the likelihood of the individual belonging to the generic index population to determine the individual's relative likelihood of a genetic match with the one or more local populations.

3. The computer-implemented method of claim 2, wherein the genetic likelihood of the individual belonging to at least one local population, is determined by comparing, using a computer, genetic markers present in the individual at a plurality of genetic loci, to the frequency of said genetic markers occurring in the at least one local population.

4. The computer-implemented method of claim 2, wherein the genetic likelihood of the individual belonging to a generic index population, is determined by comparing, using a computer, genetic markers present in the individual at a plurality of genetic loci, to the frequency of said genetic markers occurring in the generic index population.

5. The computer-implemented method of claim 2, wherein comparing the likelihood of the individual belonging to the at least one local population to the likelihood of the individual belonging to a generic index population comprises:
dividing the likelihood of the individual belonging to a first local population by the likelihood of the individual belonging to a generic index population to determine a relative likelihood ratio of the individual belonging to the first local population.

6. The computer-implemented method of claim 1, wherein the local population is defined by a method comprising using a multivariate clustering algorithm, using a computer, by separating a local population database into K groups.

7. The computer-implemented method of claim 1, wherein the generic index population is calculated, using a computer, as an average or median of all local populations in a database.

8. The computer-implemented method of claim 1, wherein the one or more additional individuals comprise one or more simulated individuals.

9. The computer-implemented method of claim 8, wherein determining one or more simulated individual's relative likelihood of having a genetic match with the local population as compared to the generic index population comprises:
generating, using a computer, a distribution of likelihood scores for population j using its observed allele frequencies.

10. The computer-implemented method of claim 9, wherein determining one or more simulated individual's relative likelihood of having a genetic match with the local population as compared to the generic index population comprises:
denoting an observed frequency of allele i on locus k in population j;
drawing an allele value for each locus using the observed frequency to create a single synthetic individual for population j; and
using the allele values to produce and retain a simulated individual's relative likelihood score.

11. The computer-implemented method of claim 10, further comprising repeating the process and determining, using a computer, individual relative likelihood scores for a large number N of synthetic individuals, and denoting the resulting score distribution as $D_N$.

12. The computer-implemented method of claim 11, wherein comparing the individual's relative likelihood to one or more simulated individual's relative likelihood comprises
determining, using a computer, a percentage of likelihood scores in $D_N$ that are lower than the individual's relative likelihood of a genetic match with a local population as compared to a generic index population.

13. The computer-implemented method of claim 1, wherein the one or more additional individuals comprise a group of actual individuals of the population.

14. A computer-implemented method of determining an individual's relative likelihood of a genetic match with one or more local European populations as compared to a generic index population comprising determining, using a computer, a genetic likelihood of the individual belonging to at least one local European population selected from a group of reference local European populations, wherein said individual's likelihood of belonging to the at least one local European population is determined from a product of the frequencies of occurrence in the local European population of genetic markers present in the individual;

determining, using a computer, a genetic likelihood of the individual belonging to a European generic index population, comprising the group of reference local European populations, wherein said individual's likelihood of belonging to a European generic index population is determined from a product of the frequencies of occurrence in the European generic index population of genetic markers present in the individual; and comparing, using a computer, the likelihood of the individual belonging to the at least one local European population to the likelihood of the individual belonging to the European generic index population to determine the individual's relative likelihood of a genetic match with the one or more local European populations;

wherein the European generic index population is an average or median of all European populations.

15. A computer-implemented method of determining an individual's relative likelihood of a genetic match with one or more local populations as compared to a generic index population comprising:

determining, using a computer, a genetic likelihood of the individual belonging to at least one local population selected from a group of reference local populations, by comparing, using a computer, genetic markers present in the individual at a plurality of genetic loci, to a product of frequencies of occurrence of said genetic markers in the at least one local population;

determining, using a computer, a genetic likelihood of the individual belonging to a generic index population comprising the group of reference local populations, by comparing, using a computer, genetic markers present in the individual at a plurality of genetic loci, to a product of frequencies of occurrence of said genetic markers in the generic index population; and comparing, using a computer, the likelihood of the individual belonging to the at least one local population to the likelihood of the individual belonging to the generic index population to determine the individual's relative likelihood of a genetic match with the one or more local populations.

16. The computer-implemented method of claim 15, wherein comparing the likelihood of the individual belonging to the at least one local population to the likelihood of the individual belonging to a generic index population comprises dividing the likelihood of the individual belonging to a first local population by the likelihood of the individual belonging to a generic index population to determine a relative likelihood ratio of the individual belonging to the first local population.

17. The computer-implemented method of claim 16, further comprising comparing, using a computer, the likelihood of the individual belonging to a second or more local population selected from a group of reference local populations, to the likelihood of the individual belonging to the generic index population to determine relative likelihood ratios of the individual belonging to each of the second or more local populations; and ranking, using a computer, the relative likelihood ratios of the individual belonging each local population.

18. The computer-implemented method of claim 16, wherein a relative likelihood ratio LR of an individual belonging to a local population as compared to a generic population is calculated by a computer using the following formula:

$$LR = \tilde{P}_j / \tilde{P}_{GI},$$

wherein $\tilde{P}_j$ is a joint probability of an individual matching a local population j, adjusted for confidence; and $\tilde{P}_{GI}$ is a joint probability of an individual matching a global index population, adjusted for confidence.

19. The computer-implemented method of claim 15, wherein the genetic likelihood of the individual belonging to at least one local population is determined by a method comprising:

extracting from a computer database, frequencies p matching the individual's allele w, w=1..2*N, where 2*N is a number of alleles tested for the individual, for each local population; and determining, using a computer, a joint probability $P_j$ of an individual matching a local population j by multiplying the extracted frequencies $p_{w|j}$ using the following formula $$P_j = \prod_{w=1}^{2N} p_{w|j}.$$

20. The computer-implemented method of claim 19, further comprising adjusting the joint probability $P_j$ for confidence, using a computer.

21. The computer-implemented method of claim 20, wherein the joint probability Pj of an individual matching a local population j, is adjusted by determining, using a computer, a lower bound of a confidence interval to arrive at a joint matching probability $\tilde{P}_j$, wherein the joint matching probability $\tilde{P}_j$ is determined by a computer using the following formula:

$$\tilde{P}_j = \exp\left\{\log P_j - Z_C \sqrt{\frac{1}{n_j} \sum_{w=1}^{2N} \frac{1 - p_{w|j}}{p_{w|j}}}\right\}$$

wherein $p_{w|j}$ is a frequency of the individual's allele value at allele locus w in population j, w=1..2*N, where 2*N is the number of alleles tested for the individual, $n_j$ is the number of individuals in population j for which genetic data were collected, and $Z_C$ is a z-score corresponding to the C confidence level.

22. The computer-implemented method of claim 15, wherein the genetic likelihood of the individual belonging to a generic index population is determined, using a computer, by a method comprising:

extracting from a computer database, frequencies p matching the individual's allele w, w=1..2*N, where 2*N is a number of alleles tested for the individual, for the generic index population GI; and determining, using a computer, a joint probability $P_{GI}$ of an individual matching the generic index population by multiplying the extracted frequencies $p_{w|GI}$ using the following formula $$P_{GI} = \prod_{w=1}^{2N} p_{w|GI}.$$

23. The method of claim 22, further comprising adjusting the joint probability $P_{GI}$ for confidence, using a computer.

24. The computer-implemented method of claim 23, wherein the joint probability of an individual matching a global population $\tilde{P}_{GI}$, as adjusted by determining the lower bound of a confidence interval, is determined by a computer using the following formula:

$$\tilde{P}_{GI} = \exp\left\{\log P_{GI} - Z_C \sqrt{\frac{1}{n_{GI}} \sum_{w=1}^{2N} \frac{1 - p_{w|GI}}{p_{w|GI}}}\right\}$$

wherein $P_{GI}$ is the joint probability of an individual matching the generic index population, $p_{w|GI}$ is a frequency of matching the individual's allele w, w=1.2*N, where 2*N is the number of alleles tested for the individual, and $n_{GI}$ is determined by the following formula:

$$n_{GI} = \frac{1}{K} \sum_{j=1}^{K} n_j$$

where K is a number of local populations used to calculate the generic index population, and $n_j$ is a number of individuals comprising local population j.

25. The computer-implemented method of claim 15, wherein the genetic markers in the individual are determined, using a computer, by sequencing the individual's autosomal DNA for N alleles, wherein N is any positive integer.

26. The computer-implemented method of claim 15, wherein the genetic markers in the individual are determined, using a computer, by sequencing the individual's autosomal STR DNA for N, wherein N is any positive integer.

27. The computer-implemented method of claim 15, wherein the genetic markers in the individual are determined, using a computer, by sequencing the individual's autosomal SNP DNA for N, wherein N is any positive integer.

28. The computer-implemented method of claim 15, wherein the local population is defined by a method comprising using a multivariate clustering algorithm, using a computer, by separating a local population database into K groups.

29. The computer-implemented method of claim 15, wherein the generic index population is calculated, using a computer, as an average or median of all local populations in a database.

30. The computer-implemented method of claim 15, wherein a first likelihood is determined of the individual belonging to a first local population selected from a group of reference local populations, and a second likelihood is determined of the individual belonging to a second local population selected from the group of reference local populations, further comprising comparing, using a computer, the first likelihood to the second likelihood to determine a relative likelihood of the individual belonging to the first local population as compared to the second local population.

31. The computer-implemented method of claim 15, wherein the local population is a world region population and the generic index population is an average or median of all world region populations.

32. The computer-implemented method of claim 15, wherein the frequency of genetic markers occurring in the generic index population is determined by a method comprising determining, using a computer, frequencies of N alleles for multiple local populations and averaging or determining the median of frequencies for each allele for all of the multiple local populations.

33. The computer-implemented method of claim 15, wherein each local population of is a breed of organisms, and the generic index population is a species of organisms.

34. The computer-implemented method of claim 33, wherein the individual is an individual dog, each local population is a breed of dogs, and the generic index population is dogs.

35. The computer-implemented method of claim 15, wherein the generic index population is selected from the group consisting of a kingdom, phylum, class, order, family, genus, species, and any subdivisions thereof.

36. A computer-implemented method comprising
(a) determining, using a computer, an individual's relative likelihood of a genetic match with a local population as compared to a generic index population; comprising:
determining, using a computer, a genetic likelihood of the individual belonging to at least one local population selected from a group of reference local populations, by comparing genetic markers present in the individual at a plurality of genetic loci, to a product of frequencies of occurrence of said genetic markers in the at least one local population;
determining, using a computer, a genetic likelihood of the individual belonging to a generic index population, said generic index population comprising the group of reference populations by comparing, using a computer, genetic markers present in the individual at a plurality of genetic loci, to a product of frequencies of occurrence of said genetic markers occurring in the generic index population; and
comparing, using a computer, the likelihood of the individual belonging to the at least one local population to the likelihood of the individual belonging to the generic index population;
(b) determining, using a computer, one or more additional individual's relative likelihood of having a genetic match with the local population as compared to the generic index population, by generating a distribution of likelihood scores for population j using the population's allele frequencies; wherein said one or more additional individuals are selected from actual individuals or simulated individuals; and
(c) comparing, using a computer, the individual's relative likelihood to the one or more additional individual's relative likelihood.

37. The computer-implemented method of claim 36, wherein determining one or more simulated individual's relative likelihood of having a genetic match with the local population as compared to the generic index population comprises:

denoting an observed frequency of allele i on locus k in population j;

drawing an allele value for each locus using the observed frequency to create a single synthetic individual for population j; and using the allele values to produce and retain a simulated individual's relative likelihood score.

38. The computer-implemented method of claim 37, further comprising repeating the process and determining, using a computer, individual relative likelihood scores for a large number N of synthetic individuals, and denoting the resulting score distribution as $D_N$.

39. The computer-implemented method of claim 38, wherein comparing the individual's relative likelihood to one or more simulated individual's relative likelihood comprises determining, using a computer, a percentage of likelihood scores in $D_N$, that are lower than the individual's relative likelihood of a genetic match with a local population as compared to a generic index population.

40. An apparatus comprising a server comprising software capable of performing the method of claim 1.

41. The apparatus of claim 40, wherein the one or more additional individuals are simulated individuals, and wherein determining at least one simulated individual's relative likelihood of having a genetic match with the local population as compared to the generic index population comprises generating a distribution of likelihood scores for population j using its observed allele frequencies.

42. A system comprising a server coupled to a database;

wherein said database includes information regarding genetic markers occurring in at least one local population selected from a group of reference local populations, and information regarding genetic markers occurring in a generic index population comprising the group of reference populations; and wherein the server comprises software capable of performing the method of claim 1.

43. A non-transitory machine-readable medium comprising code segments embodied on a medium that, when read by a machine, cause the machine to perform the method of claim 1.

44. The non-transitory machine-readable medium of claim 43, wherein the medium is a physical computer readable medium and the code segments comprise a program for performing the method of claim 1.

45. A kit comprising:

at least one device for determining genetic markers of an individual; and a physical machine readable medium comprising a medium; and a program capable of performing the method of claim 1.

* * * * *